(12) United States Patent
Halling et al.

(10) Patent No.: US 8,034,577 B2
(45) Date of Patent: Oct. 11, 2011

(54) METHODS AND PROBES FOR DETECTING ESOPHAGEAL CANCER

(75) Inventors: Kevin Halling, Rochester, MN (US); Larry E. Morrison, Glen Ellyn, IL (US); Shannon Brankley, Rochester, MN (US)

(73) Assignees: Mayo Foundation for Medical Education and Research, Rochester, MN (US); Abbott Laboratories, Inc., Des Plaines, IL (US)

( * ) Notice: Subject to any disclaimer, the term of this patent is extended or adjusted under 35 U.S.C. 154(b) by 0 days.

(21) Appl. No.: 11/356,786

(22) Filed: Feb. 17, 2006

(65) Prior Publication Data
US 2006/0211019 A1 Sep. 21, 2006

Related U.S. Application Data

(60) Provisional application No. 60/654,742, filed on Feb. 18, 2005.

(51) Int. Cl.
*G01N 33/53* (2006.01)
(52) U.S. Cl. ...................................... 435/7.23; 536/24.3
(58) Field of Classification Search .................. None
See application file for complete search history.

(56) References Cited

U.S. PATENT DOCUMENTS

| 5,491,224 A | 2/1996 | Bittner et al. |
|---|---|---|
| 5,756,696 A | 5/1998 | Gray et al. |
| 6,174,681 B1 | 1/2001 | Halling et al. |
| 6,376,188 B1 | 4/2002 | Halling et al. |

FOREIGN PATENT DOCUMENTS

WO 02/066685 A1 8/2002

OTHER PUBLICATIONS

Riegman et al. (Cancer Research vol. 61,pp. 3164-3170, 2001).*
Barrett et al. (PNAS vol. 101, pp. 17765-17770, Dec. 2004).*
Wang et al. (Acta Cytologica vol. 35, pp. 199-203, 1991). Abstract only.*
van Dekken et al. (Cancer Research, vol. 59, pp. 748-752, 1999).*
Molecular Cytogenetics : Protocols and Applications (2002),Y.-S. Fan, Ed., Chapter 2, "Labeling Fluorescence in Situ Hybridization Probes for Genomic Targets," L. Morrison et al., p. 21-40, Humana Press.

Sokolova IA, et al., The development of a multitarget, multicolor fluorescence in situ hybridization assay for the detection of urothelial carcinoma in urine, J. Molecular Diagnostics, 2:116-123, 2000.
Riegman, P.H.J. et al. Genomic alterations in malignant transformation of Barrett's esophagus. Cancer Res. Apr. 1, 2001;61(7):3164-70.
Krishnadath K.K. et al. Detection of genetic changes in Barrett's adenocarcinoma and Barrett's esophagus by DNA in situ hybridization and immunohistochemistry.Cytometry. Feb. 1, 1994;15 (2):176-84.
Ishizuka T. et al. Gene amplification profiling of esophageal squamous cell carcinomas by DNA array CGH. Biochem Biophys Res Commun. Aug. 9, 2002;296(1):152-5.
Mimori K. et al. Clinical significance of the overexpression of the candidate oncogene CYP24 in esophageal cancer. Ann Oncol. Feb. 2004;15(2):236-41.
Fahmy, Mona et al: "Chromosomal gains and genomic loss of p53 and p16 genes in Barrett's esophagus detected by fluorescence in situ hybridization of cytology specimens." Modern Pathology: An Official Journal of the United States and Canadian Academy of Pathology, Inc. May 2004, vol. 17, No. 5, pp. 588-596.
Krishnadath, Sheila et al: "Detection of cytogenetic abnormalities by multi-color FISH in brush cytology specimens of Barrett's estophagus". Gastroenterology, Elsevier, Philadelphia, PA, vol. 122, No. 4 Suppl. 1, Apr. 1, 2002, p. A289.
El Gabry E A et al: "Chromosome and gene copy alterations in Barrett's Esophagus (BE)-Associated superficial esophageal adenocarcinoma: Fluorescence in Situ Hybridization (FISH) study" Modern Pathology, vol. 18, No. Suppl. Jan. 1, 2005, p. 102A & 94th Annual Meeting of the United States and Canadian Academy of Pathology; San Antonio, TX, USA; Feb. 26-Mar. 4, 2005.
De Pender A M G et al: "Evaluationof oncogene amplification in intact and truncated cell nuclei of gastro-esophageal cancer cell lines by DNA in situ hybridisation", ACTA Histochemica, Elsevier, vol. 103, No. 2, Jan. 1, 2001, pp. 127-138.

* cited by examiner

*Primary Examiner* — Laura B Goddard
*Assistant Examiner* — Meera Natarajan
(74) *Attorney, Agent, or Firm* — Pierce Atwood LLP; Kevin M. Farrell; David J. Wilson

(57) ABSTRACT

Probe sets and methods of using probes and probe sets for selectively detecting high grade dysplasia and esophageal adenocarcinoma or low grade dysplasia from biologic samples are described. Methods of the invention include contacting a biological sample obtained from a subject with a set of chromosomal probes to selectively detect an esophageal carcinoma or precursor lesion in the sample, if any, under conditions for specifically hybridizing the probes to their nucleic targets present in the sample. The presence or absence of high grade dysplasia and esophageal adenocarcinoma or low grade dysplasia is thereafter specifically determined from the hybridization pattern detected for the set of chromosomal probes to the biological sample.

16 Claims, 6 Drawing Sheets

Figure 1A. Average percentage of cells with gain at each locus and loci ratio for each histological category.

⊚ Squamous Appearing Cell (Do Not Enumerate)

⊙ Inflammatory Appearing Cell (Do Not Enumerate)

⦚ Columnar Appearing Cell (Enumerate)

METHODS AND PROBES FOR DETECTING ESOPHAGEAL CANCER

BACKGROUND OF THE INVENTION

It is estimated that there will be 14,250 new cases and approximately 13,300 deaths from esophageal cancer in the United States during 2004. Approximately 80% of these tumors will be esophageal adenocarcinoma (EA) and the remaining 20% will be squamous cell carcinoma. The majority, if not all, of EA are thought to arise in patients with Barrett's esophagus (BE), a pre-neoplastic condition caused by metaplasia of the normal squamous mucosa of the distal esophagus into specialized intestinal mucosa containing goblet cells. BE is caused by chronic gastroesophageal reflux disease (GERD), a disorder that affects more than 20 million Americans on a daily basis. Six to fourteen percent of people with chronic GERD will develop BE. The incidence of EA in patients with BE has been reported to be approximately 0.5%-1.0% per year and the lifetime cancer risk for patients with BE is about 5%.

The histologic steps leading to esophageal adenocarcinoma in patients with BE are as follows: 1) intestinal metaplasia (IM) of the normal stratified squamous epithelium, 2) low-grade dysplasia (LGD), 3) high-grade dysplasia (HGD) and 4) EA. Patients diagnosed with BE should undergo regular surveillance for the development of neoplastic lesions, including LGD, HGD, and EA. Patients with EA and HGD must be treated aggressively either with distal esophagectomy or more recently developed therapies such as photodynamic therapy or other ablative techniques to prevent progression to metastatic and incurable disease. Patients with LGD are at risk of progressing to HGD and therefore require regular surveillance but not esophagectomy. The overall 5-year survival for patients with EA is only 20%. Early and accurate detection and treatment of the neoplastic precursors of EA (i.e., IM, LGD, and HGD) will be required if there is to be an increase in the survival rate of patients with BE-associated neoplasia.

Histology results are currently considered the gold standard for determining if a patient has dysplasia and/or EA. It is presently recommended that BE patients be monitored for the development of HGD and EA by performing regular endoscopic examinations of the esophagus and obtaining four-quadrant biopsies for every 1-2 cm of affected esophagus. However, this recommendation is not frequently followed mainly due to the extended length of time needed to perform this procedure, especially on patients with long segment BE. Problems associated with the use of biopsies for monitoring Barrett's patients for the development of neoplasia include: 1) limited sampling of affected mucosa, 2) impracticability of taking four-quadrant biopsies every 1-2 cm, and 3) poor interobserver reproducibility of pathologists for the diagnosis of LGD and HGD. It has been estimated that endoscopic surveillance protocols that utilize four-quadrant biopsies every cm only sample about 1-2% of the affected mucosa. This limited sampling may lead to false negative pathology results or to under-staging (e.g., pathology results showing only IM or LGD in a patient who has HGD or EA). Thus, there is a need for improved methods and compositions for distinguishing HGD and EA from LGD+IM+normal and LGD from normal+IM patient samples.

SUMMARY OF THE INVENTION

It is an object of the invention to provide a method for screening for an esophageal carcinoma or precursor lesion in a subject. The method involves the use of in situ hybridization for detecting chromosomal abnormalities associated with an esophageal carcinoma or precursor lesion. In this method, a set of labeled nucleic acid probes are hybridized to esophageal cells in a sample to selectively detect an esophageal carcinoma and/or precursor lesion in the sample. The hybridization pattern of the probes are then assessed and thereafter correlated with the presence or absence of an esophageal carcinoma and/or precursor lesion.

It is a further object of the present invention to provide a set of nucleic acid probes for use in the method of the present invention. The set of probes is characterized by the ability to selectively detect an esophageal carcinoma and/or precursor lesion in the biological sample. The set comprises chromosomal probes complementary to target regions bearing chromosomal abnormalities associated with low-grade dysplasia (LGD) or high-grade dysplasia (HGD) and esophageal adenocarcinoma (EA). Individual multi-probe sets may be used not only to detect LGD, HGD, and EA but also to discriminate HGD+EA from LGD+normal+IM and LGD from normal+IM.

Suitable probes for use in conjunction with the present invention include locus-specific identifier probes and chromosome enumeration probes. A probe set of the present invention may comprise chromosomal probes selected from the group consisting of an 8q24.12-13 locus-specific probe, a 7p12 locus-specific probe, a 17q11.2-12 locus-specific probe, a 20q13 locus-specific probe, a chromosome 9 enumeration probe, a chromosome 7 enumeration probe, a 5q21-22 locus-specific probe, a 5p15 locus-specific probe, a 17p13.1 locus-specific probe, a chromosome 17 enumeration probe, and a 9p21 locus-specific probe. The probe set may further comprise a chromosome Y enumeration probe.

Combinations of individual probes within a probe set of the present invention are to be chosen for combined sensitivity and specificity when used in the methods of the present invention. Chromosomal probes that detect the most frequent chromosomal losses or gains associated with an esophageal carcinoma and/or dysplasia are to be chosen, as are probes that complement one another based on sensitivity, specificity, and detectability. In this invention, probe sets chosen for the identification of LGD will have DFI values that are at most about 0.7. Probe sets chosen for the identification of HGD+EA will have DFI values that are at most about 0.5. In either case, DFI values of less than 0.5 usually provide even better results while DFI values of at most about 0.35 usually provide even better results.

DETAILED DESCRIPTION OF THE INVENTION

Figure 1A:
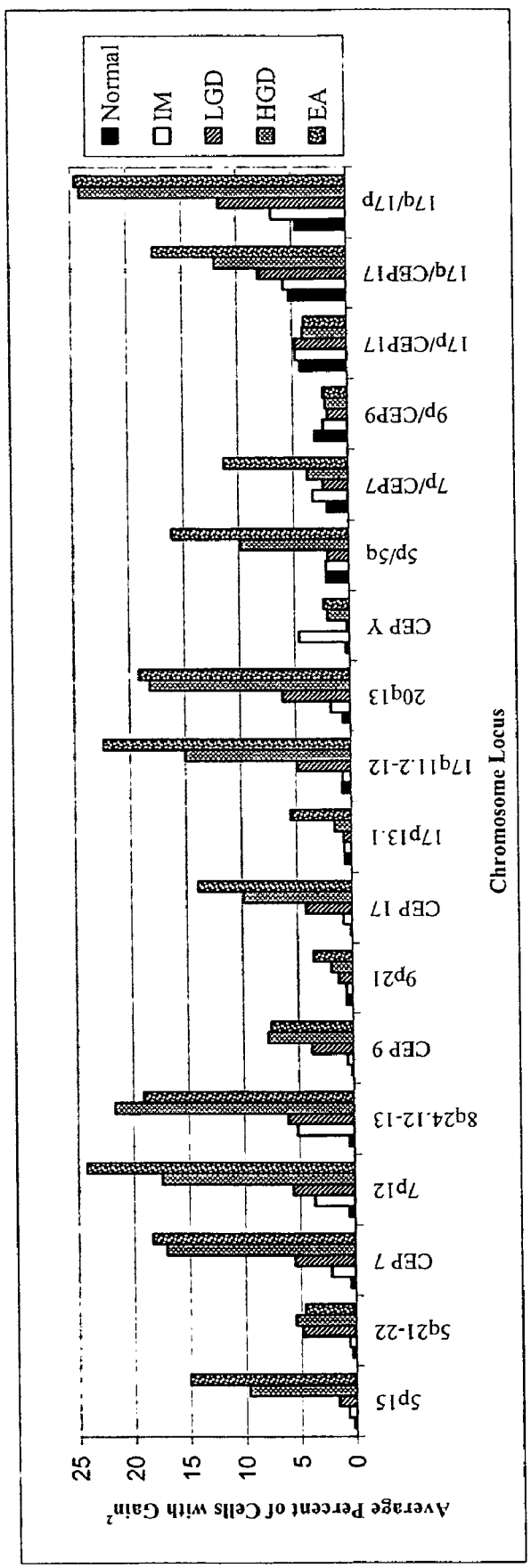
FIGS. 1A and 1B show the average percentages of cells exhibiting locus gain or loss, respectively, for each histologic category.

The present invention is based in part on the discovery that individual multi-probe sets are able to detect an esophageal carcinoma or precursor lesion with high sensitivity and specificity. The present invention includes compositions and methods for the use of such probe sets, which comprise chromosomal probes complementary to target regions bearing chromosomal abnormalities in low-grade dysplasia (LGD), high-grade dysplasia (HGD), or esophageal adenocarcinoma (EA). The individual multi-probe sets of the present invention provide higher sensitivities and specificities than individual probes, and hence probes within each set collectively comprise a better indicator of an esophageal carcinoma or precursor lesion than each individual probe contained within the set. A probe set of the present invention provides for the accurate discrimination of dysplasia and/or adenocarcinoma. Prior to the present invention, probe sets with the ability to selectively detect esophageal carcinoma or precursor lesions with high specificity and sensitivity had not been reported.

The present invention is also based in part on the finding that individual multi-probe sets may be used not only to detect LGD, HGD, and EA but also to discriminate HGD and EA from LGD+IM+normal as well as LGD from IM and normal. The methods and probe sets of the present invention allow for the early and accurate detection of EA and/or its neoplastic precursors. Discrimination is an important tool for determining appropriate treatment and preventing progression of the disease to an incurable state (see Background of the Invention).

The term "esophageal carcinoma" in the context of the present invention is intended to include intramucosal carcinoma and esophageal adenocarcinoma, or esophageal cancer. The term "precursor lesion" is intended to include low- and high-grade dysplasia as determined by histological analysis. The term "target region" or "nucleic acid target" refers to a nucleotide sequence that resides at a specific chromosomal location whose loss or gain is indicative for the presence of an esophageal carcinoma and/or precursor lesion. The "target region" or "nucleic acid target" is to be specifically recognized by a probe of the present invention and hybridize to the same in the method of the present invention.

Chromosomal Probes

Probes of the present invention are to be used in conjunction with in situ hybridization technology, or more preferably fluorescence in situ hybridization (FISH) technology, the methods of which are well known in the art. In this technology, labeled nucleic acid probes are hybridized in situ to their respective complementary nucleic acid targets in a biological sample in which identification of the presence or absence of an esophageal carcinoma or precursor lesion is desired. Subsequent detection of the probes in the sample is then correlated with a clinical diagnosis of dysplasia or cancer in the subject.

The term "chromosomal probe" or "chromosomal probe composition" is intended to mean a polynucleotide or a mixture of polynucleotides with the ability to specifically hybridize to a chromosomal region. The chromosomal region, also referred to as the probe target, may vary in length from probe to probe, ranging typically from about 70,000 nucleotides to about 800,000 nucleotides, although probe targets as small as several thousand nucleotides have been detected, and some probe targets including the repetitive sequence targets may run several megabases in size. Chromosomal probes are often comprised of polynucleotide fragments ranging in size from about 50 to about 1,000 nucleotides in length, and are only restricted by their ability to specifically detect a region of interest. Locus-specific probe targets preferably comprise at least 100,000 nucleotides. A chromosomal probe of the present invention has been combined or associated with individual moieties enabling detection.

Suitable probes for use in conjunction with the present invention include locus-specific identifier probes and chromosome enumeration probes. A locus-specific probe for in situ hybridization recognizes and binds to a specific non-repetitive locus whose genetic aberration is correlated with EA and/or dysplasia. The probe may target coding or non-coding regions, or both, including exons, introns, and/or regulatory sequences controlling gene expression or processing of gene products of a targeted region. When targeting of a particular gene locus is desired, probes that hybridize along the entire length of the targeted gene are preferred although not required. For cells of a given sample relative to those of a control, increases or decreases in the number of signals for a probe indicate a gain or loss, respectively, for the corresponding region. Although not required, a locus-specific probe may include an oncogene or tumor suppressor gene, the genetic aberration of which is correlated with an esophageal carcinoma or dysplasia. Probes, which hybridize to regions comprising such loci, include, for example, 8q24.12-13, 9p21, 17q11.2-12, and 20q13, which hybridize respectively to C-MYC, P16 (a tumor suppressor gene), HER2 (an oncogene), and ZNF217 (also an oncogene). Other locus specific probes of the present invention may include for example a 17p13.1 (P53) locus-specific probe, a 7p12 (EGFR) locus-specific probe, a 5q21-22 (APC) locus-specific probe, and a 5p15 locus-specific probe.

A chromosome enumeration probe is any probe able to enumerate the number of specific chromosomes in a cell. A chromosome enumeration probe typically recognizes and binds to a region near to (referred to as "peri-centromeric") or at the centromere of a specific chromosome, typically a repetitive DNA sequence. Enumeration of chromosomes is possible in this case since loss of a centromeric region almost always leads to loss of the entire chromosome. Deletion or amplification of a particular chromosomal region can be differentiated from loss or gain of the whole chromosome (aneusomy), within which it normally resides, by comparing the number of signals corresponding to the particular locus (copy number) to the number of FISH signals for the corresponding centromere. One method for making this comparison is to divide the number of signals representing the locus by the number of signal representing the centromere. Ratios less than one indicate deletion of the locus, and ratios greater than one indicate gain of the locus. Similarly, comparison can be made between two different loci on the same chromosome, for example on two different arms of the chromosome, to indicate imbalanced gains or losses within the chromosome. In lieu of a centromeric probe for a chromosome, one of skill in the art will recognize that a chromosomal arm probe may alternately be used to approximate whole chromosomal loss or gain. However, such probes are not as accurate at enumerating chromosomes since the loss of signals for such probes may not always indicate a loss of the entire chromosomes. Examples of chromosome enumeration probes include CEP® probes (e.g., CEP 12 and X/Y probes) commercially available from Vysis, Inc., Downers Grove, Ill.

A probe set of the present invention may comprise chromosomal probes selected from the group consisting of an 8q24.12-13 locus-specific probe, a 7p12 locus-specific probe, a 17q11.2-12 locus-specific probe, a 20q13 locus-specific probe, an enumeration probe for chromosome 9, a chromosome enumeration probe for chromosome 7, a 5q21-22 locus-specific probe, a 5p15 locus-specific probe, a 17p13.1 locus-specific probe, a chromosome enumeration probe for chromosome 17, and a 9p21 locus-specific probe. The probe set may further comprise a chromosome enumeration probe for chromosome Y. In a preferred embodiment, the set may comprise a 20q13 locus-specific probe, a 17q11.2-12 locus-specific probe, a 9p21 locus-specific probe, and an 8q24.12-13 locus-specific probe.

Individual probes commonly appearing in probe sets which are able to discriminate LGD from IM+normal include a chromosome enumeration probe for chromosome 7, a chromosome enumeration probe for the Y chromosome and a 9p21 locus-specific probe. Individual probes commonly appearing in probe sets which are able to discriminate HGD and EA from LGD+normal+IM include a 5p15 locus-specific probe, an 8q24.12-13 locus-specific probe, 7p12 locus-specific probe, 5q21-22 locus-specific probe, a 9p21 locus-specific probe, a chromosome enumeration probe for chromosome 17, a chromosome 9 enumeration probe, a 17p13.1 locus-specific probe, a 17q11.2-12 locus-specific probe and a 20q13 locus-specific probe.

A probe set able to detect LGD and/or discriminate LGD from IM+normal may comprise a) a 9p21 locus-specific probe; b) a chromosome enumeration probe for chromosome 9; and c) a chromosome enumeration probe for chromosome 7. The set may comprise a) a 9p21 locus-specific probe; b) a chromosome enumeration probe for chromosome 7; and c) a 5q21-22 locus-specific probe. The set may comprise a) a 9p21 locus-specific probe; b) a chromosome enumeration probe for chromosome 7; and c) a 5p15 locus-specific probe. The set may comprise a) a 17q11.2-12 locus-specific probe; b) a 9p21 locus-specific probe; and c) a chromosome enumeration probe for chromosome 7. The set may comprise a) a 20q13 locus-specific probe; b) a 9p21 locus-specific probe; and c) a chromosome enumeration probe for chromosome 7. The set may comprise a) a 9p21 locus-specific probe; b) a 7p12 locus-specific probe; and c) a chromosome enumeration probe for chromosome 7. The set may comprise a) a 9p21 locus-specific probe; b) a chromosome enumeration probe for chromosome 17; and c) a chromosome enumeration probe for chromosome 7. The set may comprise a) a 9p21 locus-specific probe; b) a chromosome enumeration probe for chromosome 7; and c) a chromosome enumeration probe for chromosome 9. The set may comprise a) a 17p13.1 locus-specific probe; b) a 9p21 locus-specific probe; and c) a chromosome enumeration probe for chromosome 7. The set may comprise a) an 8q24.12-13 locus-specific probe; b) a 9p21 locus-specific probe; and c) a chromosome enumeration probe for chromosome 7. Any of the sets able to detect LGD and/or discriminate LGD from IM may further comprise a chromosome enumeration probe for the Y chromosome.

A probe set able to detect HGD/EA and/or discriminate HGD/EA from LGD+IM+normal may comprise a) a 20q13 locus-specific probe; b) a chromosome enumeration probe for chromosome 9; c) a 7p12 locus-specific probe; and d) a 5q21-22 locus-specific probe. The set may comprise a) a 17p13.1 locus-specific probe; b) a chromosome enumeration probe for chromosome 9; c) a 17q11.2-12 locus-specific probe; and d) a 5p15 locus-specific probe. The set may comprise a) a 17p13.1 locus-specific probe; b) a 20q13 locus-specific probe; c) a 17q11.2-12 locus-specific probe; and d) a 5p15 locus-specific probe. The set may comprise a) a chromosome enumeration probe for chromosome 9; b) an 8q24.12-13 locus-specific probe; c) a 7p12 locus-specific probe; and d) a 5q21-22 locus-specific probe. The set may comprise a) a chromosome enumeration probe for chromosome 9; b) a 7p12 locus-specific probe; c) a 5p15 locus-specific probe; and d) a 5q21-22 locus-specific probe. The set may comprise a) a 17p13.1 locus-specific probe; b) a 17q11.2-12 locus-specific probe; c) a 5p15 locus-specific probe; and d) a 5q21-22 locus-specific probe. The set may comprise a) a 17p13.1 locus-specific probe; b) a 20q13 locus-specific probe; c) a 17q11.2-12 locus-specific probe; and d) a 9p21 locus-specific probe. The set may comprise a) a 17p13.1 locus-specific probe; b) a 17q11.2-12 locus-specific probe; c) a chromosome enumeration probe for chromosome 17; and d) a 5p15 locus-specific probe. The set may comprise a) a 17p13.1 locus-specific probe; b) a 17q11.2-12 locus-specific probe; c) an 8q24.12-13 locus-specific probe; and d) a 5p15 locus-specific probe. The set may comprise a) a 17p13.1 locus-specific probe; b) a 17q11.2-12 locus-specific probe; c) a 7p12 locus-specific region; and d) a 5p15 locus-specific probe. The set may comprise a) a 17p13.1 locus-specific probe; b) a 17q11.2-12 locus-specific probe; c) a chromosome enumeration probe for chromosome 7; and d) a 5p15 locus-specific probe. The set may comprise a) a 20q13 locus-specific probe; b) a 17q11.2-12 locus-specific probe; c) an 8q24.12-13 locus-specific probe; and d) a 5p15 locus-specific probe. The set may comprise a) a 20q13 locus-specific probe; b) a 17q11.2-12 locus-specific probe; c) a 9p21 locus-specific probe; and d) an 8q24.12-13 locus-specific probe. The set may comprise a) a 17p13.1 locus-specific probe; b) a 20q13 locus-specific probe; c) a 17q11.2-12 locus-specific probe; and d) a 9p21 locus-specific probe. The set may comprise a) a 20q13 locus-specific probe; b) a 17q11.2-12 locus-specific probe; c) a 7p12 locus-specific probe; and d) a 5p15 locus-specific probe. The set may comprise a) a 20q13 locus-specific probe; b) a 17q11.2-12 locus-specific probe; c) a chromosome enumeration probe for chromosome 7; and d) a 5p15 locus-specific probe. The set may comprise a) a 20q13 locus-specific probe; b) a 7p12 locus-specific probe; c) a 5q21-22 locus-specific probe; and d) a 5p15 locus-specific probe. The set may comprise a) a 17p13.1 locus-specific probe; b) a chromosome enumeration probe for chromosome 17; c) a 17q11.2-12 locus-specific probe; and d) a 5p15 locus-specific probe. The set may comprise a) a chromosome enumeration probe 17; b) a 20q13 locus-specific probe; c) a 17q11.2-12 locus-specific probe; and d) a 9p21 locus-specific probe. The set may comprise a) a 17p13.1 locus-specific probe; b) a 17q11.2-12 locus-specific probe; c) a 9p21 locus-specific probe; and d) a 5p15 locus-specific probe. The set may comprise a) a 20q13 locus-specific probe; b) a 17q11.2-12 locus-specific probe; and c) a 5p15 locus-specific probe. The set may comprise a) a 20q13 locus-specific probe; b) a 17q11.2-12 locus-specific probe; c) a 5p15 locus-specific probe; and d) a chromosome enumeration probe for the Y chromosome. The set may comprise a) a 20q13 locus-specific probe; b) a 17q11.2-12 locus-specific probe; c) a chromosome enumeration probe for chromosome 17; and d) a 9p21 locus-specific probe. The set may comprise a) a 20q13 locus-specific probe; b) a 17q11.2-12 locus-specific probe; c) a 9p21 locus-specific probe; and d) a chromosome enumeration probe for chromosome 9. The set may comprise a) a 20q13 locus-specific probe; b) a 17q11.2-12 locus-specific probe; c) a 9p21 locus-specific probe; and d) a 5q21-22 locus-specific probe. The set may comprise a) a 17p13.1 locus-specific probe; b) a 20q13 locus-specific probe; c) a chromosome enumeration probe for chromosome 17; and d) a 5p15 locus-specific probe. The set may comprise a) a 20q13 locus-specific probe; b) a 17q11.2-12 locus-specific probe; c) a chromosome enumeration probe for chromosome 17; and d) a 5p15 locus-specific probe. The set may comprise a) a 20q13 locus-specific probe; b) a 17q11.2-12 locus-specific probe; c) a 5q21-22 locus-specific probe; and d) a 5p15 locus-specific probe. The set may comprise a) a 17q11.2-12 locus-specific probe; b) a 17p13.1 locus-specific probe; c) a chromosome enumeration probe for chromosome 17; d) a 9p21 locus-specific probe; and e) an 8q24.12-13 locus-specific probe. The set may comprise a) a 17q11.2-12 locus-specific probe; b) a chromosome enumeration probe for chromosome 9; c) a 5q21-22 locus-specific probe; and d) a 5p15 locus-specific probe. The set may comprise a) a chromosome enumeration probe for chromosome 17; b) a 17q11.2-12 locus-specific probe; and c) a 5p15 locus-specific probe. The set may comprise a) a chromosome enumeration probe for chromosome 17; b) a 17q11.2-12 locus-specific probe; c) a 5p15 locus-specific probe; and d) a chromosome enumeration probe for the Y chromosome.

Chromosome enumeration probes and locus-specific identifier probes can be obtained commercially from Vysis, Inc. (Downers Grove, Ill.), Molecular Probes, Inc. (Eugene, Oreg.), or Cytocell (Oxfordshire, UK). Such probes can also be prepared using standard techniques, which are known in the art. Chromosomal probes may be prepared, for example, from peptide nucleic acids (PNAs), or from cloned human DNA such as plasmids, bacterial artificial chromosomes (BACs), and P1 artificial chromosomes (PACs) that contain inserts of human DNA sequences. A region of interest may be obtained via PCR amplification or cloning. Alternatively, chromosomal probes may be prepared synthetically.

Detection of probes of the present invention may be accomplished by any of a number of methods, which are known in the art, as long as each probe within a set, upon hybridization, is distinguishable from one another. Label containing moieties may be associated directly or indirectly with chromosomal probes. The term "label containing moiety" or "detection moiety" generally refers to a molecular group or groups associated with a chromosomal probe, either directly or indirectly, which allows for detection of that probe upon hybridization to its target. Different label containing moieties are to be chosen for each individual probe within a particular set so that each hybridized probe may be visually distinct from the others upon detection. Preferably, fluorescence in situ hybridization (FISH) is employed and the chromosomal probes are labeled with distinct fluorescent label containing moieties. Fluorophores, organic molecules that fluoresce upon irradiation at a particular wavelength, may be directly attached to the chromosomal probes. Direct-labeled FISH probes are preferred because they require less processing time then in-direct labeled probes. Also, the sheer number of fluorophores in existence allows easy visualization of many different probes within the same sample. A large number of fluorophores are commercially available in reactive forms amenable to labeling DNA containing aliphatic amine groups.

Attachment of fluorophores to nucleic acid probes is well known in the art and may be accomplished by any available means. Fluorophores may be covalently attached to a particular nucleotide, for example, and the labeled nucleotide incorporated into the probe using standard techniques such as nick translation, random priming, and PCR labeling. Alternatively, the fluorophore may be covalently attached via a linker to the deoxycytidine nucleotides of the probe that have been transaminated. Methods for labeling probes are described in U.S. Pat. No. 5,491,224 and *Molecular Cytogenetics: Protocols and Applications* (2002), Y.-S. Fan, Ed., Chapter 2, "Labeling Fluorescence In Situ Hybridization Probes for Genomic Targets," L. Morrison et al., p. 21-40, Humana Press, both references of which are herein incorporated by reference.

Fluorophores that can be used in conjunction with the present invention include for example 7-amino-4-methylcoumarin-3-acetic acid (AMCA), TEXAS RED (Molecular Probes, Inc., Eugene, Oreg.); 5-(and-6)-carboxy-X-rhodamine, lissamine rhodamine B, 5-(and-6)-carboxyfluorescein; fluorescein-5-isothiocyanate (FITC); 7-diethylaminocoumarin-3-carboxylic acid, tetramethylrhodamine-5-(and-6)-isothiocyanate; 5-(and-6)-carboxytetramethylrhodamine; 7-hydroxycoumarin-3-carboxylic acid; 6-[fluorescein 5-(and-6)-carboxamido] hexanoic acid; N-(4,4-difluoro-5,7-dimethyl-4-bora-3a, 4a diaza-3-indacenepropionic acid; eosin-5-isothiocyanate; erythrosine-5-isothiocyanate; 5-(and-6)-carboxyrhodamine 6G; and CASCADE blue aectylazide (Molecular Probes, Inc., Eugene, Oreg.).

One of skill in the art will recognize that other luminescent agents or dyes may be used in lieu of fluorophores as label containing moieties. Other luminescent agents, which may be used, include, for example, radioluminescent, chemiluminescent, bioluminescent, and phosphorescent label containing moieties. Alternatively, in situ hybridization of chromosomal probes may be employed with the use of detection moieties visualized by indirect means. Probes may be labeled with biotin or digoxygenin using routine methods known in the art, and then further processed for detection. Visualization of a biotin-containing probe may be achieved via subsequent binding of avidin conjugated to a detectable marker. The detectable marker may be a fluorophore, in which case visualization and discrimination of probes may be achieved as described above for FISH. Chromosomal probes hybridized to target regions may alternatively be visualized by enzymatic reactions of label moieties with suitable substrates for the production of insoluble color products. Each probe may be discriminated from other probes within the set by choice of a distinct label moiety. A biotin-containing probe within a set may be detected via subsequent incubation with avidin conjugated to alkaline phosphatase (AP) or horseradish peroxidase (HRP) and a suitable substrate. 5-bromo-4-chloro-3-indolylphosphate and nitro blue tetrazolium (NBT) serve as substrates for alkaline phosphatase, while diaminobenzidine serves as a substrate for HRP.

In embodiments where fluorophore labeled probes or probe compositions are utilized, the detection method can involve fluorescence microscopy, flow cytometry, or other means for determining probe hybridization. Any suitable microscopic imaging method may be used in conjunction with the methods of the present invention for observing multiple fluorophores. In the case where fluorescence microscopy is employed, hybridized samples may be viewed under light suitable for excitation of each fluorophore and with the use of an appropriate filter or filters. Automated digital imaging systems such as the MetaSystems or Applied Imaging systems may alternatively be used.

Any probe set or probe sets of the present invention may be packaged with other reagents, and optionally with instructions, as kits, which may be used in practicing the methods of the present invention. Useful kits may include one or more probe sets comprising chromosomal probes selected from the group consisting of an 8q24.12-13 locus-specific probe, a 7p12 locus-specific probe, a 17q11.2-12 locus-specific probe, a 20q13 locus-specific probe, a chromosome enumeration probe for chromosome 9, a chromosome enumeration probe for chromosome 7, a 5q21-22 locus-specific probe, a 5p15 locus-specific probe, a 17p13.1 locus-specific probe, a chromosome enumeration probe for chromosome 17, and a 9p21 locus-specific probe. The set may further comprise a chromosome enumeration probe for the Y chromosome.

In Situ Hybridization

The term "in situ" is intended to mean that chromosomes of a cell from a biological sample are exposed from the nucleus and accessible to labeled chromosomal probes, without substantial disruption or relocation of the chromosomes with respect to each other. "Hybridization" or "hybridize" is intended to refer to the formation of a specific hybrid between a probe and a target region. Typically, a hybrid is a molecule that includes a double stranded, helically configured portion comprised of complementary paired single stranded molecules, one of which comprises the nucleic acid target, and the other of which is the labeled DNA nucleotide sequence of a probe. The term "in situ hybridization" is intended to mean hybridization of a probe to a target that exists within a biological sample comprising a cytological or histological preparation or specimen. During in situ hybridization, hybrids are produced between a probe and a target. "In situ hybridization" may include denaturation prior to hybridization and hybrid or probe detection subsequent to probe hybridization to a target. A biological specimen can be adhered as a layer upon a slide surface, and a biological sample can, for example, comprise individual chromosomes or chromosome regions that have been treated to maintain their morphology under denaturing conditions, or conditions such as typically encountered in a probe detection procedure.

Probe Selection Methods

Probe sets for use in the methods of the present invention can be selected using the principles described in the examples. Combinations of chromosomal probes within a probe set are chosen for sensitivity, specificity, and detectability regarding the esophageal carcinoma and dysplasia of interest.

Sensitivity refers to the ability of a test (e.g., FISH) to detect disease (e.g., LGD, HGD or EA) when it is present. More precisely, sensitivity is defined as True Positives/(True Positives+False Negatives). A test with high sensitivity has few false negative results while a test with low sensitivity has many false negative results. Specificity, on the other hand, refers to the ability of test (e.g., FISH) to give a negative result when disease is not present. More precisely, specificity is defined as True Negatives/(True Negatives+False Positives). A test with high specificity has few false positive results while a test with a low specificity has many false positive results.

In general, chromosomal probe sets with the highest combined sensitivity and specificity for the detection of LGD and/or HGD+EA are to be chosen. The combined sensitivity and specificity of a probe set can be represented by the parameter distance from ideal (DFI). DFI values range from 0 to 1.414, with 0 representing a probe set having 100% sensitivity and 100% specificity and 1.414 representing a probe set with 0% sensitivity and 0% specificity. In this invention, probe sets chosen for the identification of LGD will have DFI values that are at most about 0.7. In this invention, probe sets chosen for the identification of HGD+EA will have DFI values that are at most about 0.5. DFI values less than about 0.5 usually provide even better results. DFI values less than about 0.35 usually provide even better results.

The number of probes within a set that is to be viewed by a human observer (and not with computer assisted imaging techniques) is restricted by the number of unique fluorophores that provide visually distinguishable signals upon hybridization. For example, at the current time it is difficult to have more than four unique fluorophores (which appear as red, green, aqua, and gold signals to the human eye) in a single probe set. The reason this is important is because the sensitivity of an assay generally increases as the number of probes within a set increases. However, the increases in sensitivity become smaller and smaller with the addition of more probes and at some point the inclusion of additional probes to a probe set is not associated with significant increases in the sensitivity of the assay ("diminishing returns"). It should also be noted that the inclusion of multiple probes in a probe set has the ability to increase the specificity of the assay. For these reasons, a probe set of the present invention preferably comprises three, or preferably four, chromosomal probes since this number provides for the desired sensitivity and specificity of detection.

Individual probes are to be chosen for inclusion in a probe set of the present invention based on their ability to complement other probes within the set. Each probe should identify a marker for an esophageal carcinoma or precursor lesion that the other probes sometime fail to identify. One method for determining which probes complement one another is to first identify single probes with the lowest DFI values on a group of tumor specimens. Then additional probes may be tested on the tumor samples that the initial probe failed to identify, and the probe with the lowest DFI value added to the set. This may then be repeated until a full set of chromosomal probes with the desired DFI value is achieved.

Discrimination analysis is one method that can be used to determine which probes are best able to detect EA and its precursor lesions. This method assesses if individual probes are able to detect a statistically different percentage of abnormal cells in test specimens (e.g., LGD, HGD, and EA) when compared to a control specimen group such as normal specimens. The detection of cells with chromosomal (or locus) gains or chromosomal (or locus) losses can both be used to identify neoplastic cells in Barrett's esophagus patients with LGD, HGD, or EA. However, chromosomal losses sometimes occur as an artifact in normal cells because of random signal overlap and/or poor hybridization. Consequently, chromosomal gains are for the most part a more reliable indicator of the presence of neoplastic cells.

Cutoff values for individual chromosomal gains and losses must be determined when choosing a probe set. The term "cutoff value" is intended to mean either the absolute number or percentage of cells in a population that have genetic aberrations (i.e., losses or gains for target regions) for a particular probe or combination of probes within a set for a positive determination to be made. If the number of cells in the specimen harboring losses or gains for a particular probe is higher than the cutoff value, the sample is determined to be positive for the applicable pathology (e.g., LGD, HGD, or EA).

Probes can be selected simply for their ability to detect EA and it's precursor lesions. However, the ability to not only collectively detect these lesions but also to discriminate one from another (e.g. the ability to discriminate LGD from HGD+EA) has potential clinical utility. To this end, analyses were performed to determine the DFI values of different probe sets for discriminating LGD specimens from IM and normal specimens and HGD and EA specimens from LGD, IM, and normal specimens.

Screening and Diagnosis of Patients for Esophageal Dysplasia and/or Carcinoma

This method comprises first obtaining a biological sample comprising esophageal cells from a subject suspected of having an esophageal carcinoma or precursor lesion. The sample is then contacted with a set of chromosomal probes to selectively detect an esophageal carcinoma or precursor lesion in the sample, if any, under conditions for specifically hybridizing the probes to their nucleic acid targets present in the sample. The probes of the set may be hybridized at one time or sequentially with the results of each hybridization imaged, the probe or probes stripped, and the sample thereafter hybridized with the remaining probe or probes. Multiple probe sets may also be hybridized to the sample in this manner. The set of chromosomal probes is chosen such that said set is able to selectively detect an esophageal carcinoma or precursor lesion in the biological sample. Any probe set of the invention may be used in conjunction with this method. This method further comprises detecting a hybridization pattern for the set of chromosomal probes to the biological sample, wherein the hybridization pattern is indicative for the presence or absence of the esophageal carcinoma or precursor lesion in the subject. In a preferred embodiment the hybridization pattern is detected via FISH, as described above.

The term "biological sample" or "specimen" is intended to mean a sample comprising esophageal cells. The biological sample may further be derived from a subject that has been diagnosed with chronic gastroesophageal reflux disease, scleroderma, esophageal adenocarcinoma, prior esophageal resection, Barrett's esophagus, or an esophageal mucosa abnormality. The biological sample may be derived from the proximal, mid, or distal esophagus.

Biological samples may be obtained using any of a number of methods in the art. Normally, the mucus layer of the esophagus will need to be cleared from the esophageal mucosa with a mucolytic agent such as n-acetyl-cysteine to allow adequate specimens to be acquired. Examples of biological samples comprising esophageal cells include those obtained from biopsies, cytologic specimens, and resected specimens. A cytologic specimen may be an endoscopic brushing specimen or a balloon cytology specimen. A biological specimen may also be embedded in paraffin and sectioned for use in the method of the present invention. Typically, biological samples, once obtained, are harvested and processed prior to hybridization using standard methods known in the art. Such processing typically includes fixation in, for example, an acid alcohol solution, acid acetone solution, or aldehyde solution such as formaldehyde and glutaraldehyde. A 3:1 ratio of methanol:glacial acetic acid is typically used. Cells may be concentrated to a desired density prior to probe hybridization.

Conditions for specifically hybridizing the probes to their nucleic acid targets generally include the combinations of conditions that are employable in a given hybridization procedure to produce specific hybrids, the conditions of which may easily be determined by one of skill in the art. Such conditions typically involve controlled temperature, liquid phase, and contact between a chromosomal probe and a target. Hybridization conditions vary depending upon many factors including probe concentration, target length, target and probe G-C content, hybridization buffer salt concentration, solvent composition, temperature, and duration of incubation. At least one denaturation step may precede contact of the probes with the targets. Alternatively, both the probe and nucleic acid target may be subjected to denaturing conditions together with subsequent contact of the probe with the biological sample. Hybridization may be achieved with subsequent incubation of the probe/sample in, for example, a liquid phase of about a 50:50 volume ratio mixture of 2-4× saline sodium citrate (SSC) and formamide, at a temperature in the range of about 25 to about 55° C. for a time that is illustratively in the range of about 0.5 to about 96 hours, or more preferably at a temperature of about 32 to about 40° C. for a time in the range of about 2 to about 16 hours. In order to increase specificity, use of a blocking agent such as unlabeled blocking nucleic acid as described in U.S. Pat. No. 5,756,696, the contents of which are herein incorporated by reference, may be used in conjunction with the methods of the present invention. Other conditions may be readily employed for specifically hybridizing the probes to their nucleic acid targets present in the sample, as would be readily apparent to one of skill in the art.

Upon completion of a suitable incubation period, chromosomal probes non-specifically bound to sample DNA may be removed by a series of washes. Temperature and salt concentrations are suitably chosen for a desired stringency. The level of stringency required depends on the complexity of a specific probe sequence in relation to the genomic sequence, and may be determined by systematically hybridizing probes to samples of known genetic composition. In general, high stringency washes may be carried out at a temperature in the range of about 65 to about 80° C. with about 0.2× to about 2×SSC and about 0.1% to about 1% of a non-ionic detergent such as Nonidet P-40 (NP40). If lower stringency washes are required, the washes may be carried out at a lower temperature with an increased concentration of salt.

After FISH hybridization has been performed, slides are assessed with a fluorescence microscope equipped with appropriate filters to determine if there are cells on the slide that have chromosomal abnormalities consistent with a diagnosis of neoplasia (which in this invention refers to the presence of cells that have chromosomal abnormalities consistent with a diagnosis of LGD, HGD, or EA). This microscopic analysis can be performed either by: 1) enumerating the signal patterns in a certain number of consecutive cells (e.g., 50 or 100 cells), excluding the cells that are clearly non-neoplastic such as inflammatory cells, or 2) scanning the slide for cells that have cytologic features (e.g., nuclear enlargement, nuclear irregularity, or mottled chromatin staining) that suggest that the cells are neoplastic and enumerating the signal patterns in just those cells. Each of these methods has advantages and disadvantages and a combination of the two may sometimes be required.

The first technique of enumerating consecutive cells may be necessary if the exact percentage of cells containing a certain abnormality must be determined to know if the case is positive for abnormality. For example to determine if a case showing homozygous or hemizygous 9p21 loss is in fact positive for LGD one would have to know the percentage of cells showing the abnormality. The first technique is also necessary if the neoplastic cells do not exhibit significant cytologic abnormalities, as is the case for LGD. The disadvantage of the first technique of enumerating consecutive cells is that it is fairly time consuming and it is therefore only practical to enumerate a relatively small number of the cells (e.g., 50 or 100 cells). The problem with this is that there are often thousands of cells on the slide and sometimes just a very small fraction of the total number of cells are actually tumor cells. Consequently, by using the first technique one risks false negative results due to limited sampling.

Fortunately, a scanning technique (technique number 2) which allows one to rapidly look at a large number of cells can be used to help avoid false negative results due to limited sampling. This technique (disclosed in U.S. Pat. No. 6,174,681, the contents of which are herein incorporated by reference) is performed by visually scanning the slide, usually the entire slide, for cells that have cytologic features suggestive though not absolutely diagnostic for neoplasia. Scanning is performed by viewing each microscopic field of view on the slide fairly rapidly, looking only for cells that have nuclear abnormalities suggestive of neoplasia. The person doing the scanning attempts to look at all fields of view on the slide but does not spend time evaluating the signals patterns of a cell or cells in a field of view unless that cell or cells has/have abnormal cytologic features. (It is sometimes asked why FISH is even necessary if the cytologic features seen by DAPI suggest that the cells are neoplastic. The reason is that while the features are suggestive they are not absolutely diagnostic of neoplasia.) As noted above, scanning allows the enumeration to be focused on the generally small fraction of cells that are likely to have chromosomal abnormalities consistent with a diagnosis of neoplasia. Scanning allows for faster analysis and increases the likelihood that a positive result will not be missed. Scanning while generally performed with a DAPI (4,6-diamidino-2-phenylindole dihydrochloride) nuclear counterstain can also be done with other counterstains such as propidium iodide. Propidium iodide, typically used at a concentration of about 0.4 µg/ml to about 5 µg/ml, is a red-fluorescing DNA-specific dye that can be observed at an emission peak wavelength of 614 nm. DAPI, typically used at a concentration of about 125 ng/ml to about 1000 ng/ml, is a blue fluorescing DNA-specific stain that can be observed at an emission peak wavelength of 452 nm The hybridization pattern for the set of chromosomal probes is detected and recorded for cells chosen for assessment of chromosomal losses and/or gains. Hybridization is detected by the presence or absence of the particular signals generated by each of the chromosomal probes. The term "hybridization pattern" is intended to refer to the quantification of the number of chromosomal hybridization signals for each of the probe signals for those cells chosen for such assessment by one of the two techniques described above. Once the number of target regions within each cell is determined, as assessed by the number of regions showing hybridization to each probe, relative chromosomal gains and/or losses may be quantified. For probes that hybridize to an autosome, more than two probe signals per cell is considered a gain while less than two is considered a loss. For a chromosome enumeration probe for the Y chromosome, more than one probe signal per cell in males is considered a gain while less than one probe signal per cell is considered a loss. The percentages of cells with gain and/or loss (abnormal cells) are to be recorded for each locus. A sample may be considered positive for abnormality (e.g., LGD, HGD, or EA) if the percentage of abnormal cells with respect to any of the tested loci exceeds the cutoff value for that locus.

It is not possible to determine the exact percentage of cells showing abnormality with the scanning technique since the person doing the analysis does not keep track of the exact number of total cells that have been assessed by scanning (often in the thousands). However, it is not necessary to know the exact number of cells viewed on the slide with the scanning technique since the cells that are being looked for (namely cells that show marked chromosomal abnormalities such as polysomy) are virtually diagnostic of the presence neoplasia regardless of the total number of cells present on the slide. In other words, when using the scanning technique, it is the absolute number of cells showing abnormality rather than the percentage of cells showing abnormality that is used to determine if a case is positive or negative for neoplasia. Previous studies by our group and others have demonstrated that as few as four abnormal cells (regardless of the total number of normal appearing cells on the slide) with polysomy (i.e., a cell that shows gains for two or more probes) is sufficient to confidently call a case positive for abnormality (see, Sokolova I A, et al., J. Molecular Diagnostics, 2000).

As noted above, the inclusion of multiple probes in a single probe set increases the sensitivity of the assay over that obtained with a single probe. However, this increase in sensitivity can be accompanied by a loss of specificity since the chances that any of the multiple probes will give a false positive result increases. To maintain high specificity, one can develop stringent cutoff criteria for cells showing abnormality of a single locus. For example, one could stipulate that at least 30% of the cells have to show homozygous 9p21 loss to call a case positive for abnormality. Additionally, for cases not exceeding these cutoffs for single probes it can be stipulated that two or more loci demonstrate gain or loss within the same cell in order to consider that cell abnormal, and an appropriate cutoff then applied to establish whether or not the specimen was positive. For example, wherein gains are indicative of an esophageal malignancy or precursor lesion, a sample could be considered positive if it contains, for example, at least four cells showing gains of at least two or more target regions (see, Sokolova I A, et al, J. Molecular Diagnostics, 2000).

More specifically, for example, specimens were considered positive if they fulfilled the following criteria:

≧13% of cells exhibiting hemizygous and/or homozygous 9p21 loss (most consistent with a diagnosis of low-grade dysplasia)

≧4% of cells exhibiting gain of 8q24 (most consistent with a diagnosis of high-grade dysplasia/adenocarcinoma)

≧8% of cells exhibiting gain of 17q11 (most consistent with a diagnosis of high-grade dysplasia/adenocarcinoma)

≧12% of cells exhibiting gain of 20q13 (most consistent with a diagnosis of high-grade dysplasia/adenocarcinoma). In a more preferred embodiment, ≧16% of cells exhibiting gain of 20q13 (most consistent with a diagnosis of high-grade dysplasia/adenocarcinoma)

≧3% of cells exhibiting polysomy (most consistent with a diagnosis of high-grade dysplasia/adenocarcinoma)

The numbers and probes given above are only exemplary. One practiced in the art will see that lesser or greater levels of sensitivity and specificity can be had depending on the criteria and the probe set used for the particular assay being run. For example, a lower sensitivity but higher specificity could be obtained if a greater percentage of cells with 'polysomy' (e.g., ≧5%) was utilized as a cutoff for abnormality.

EXEMPLIFICATION

Example 1

Probe Selection
FISH Probe Sets

FISH was performed with three unique probe sets. Each probe set contained four chromosome enumeration probes (CEP®) or locus specific identifiers (LSI®) to centromeres or specific loci of chromosomes that have been shown to be frequently altered in patients with BE-associated neoplasia (Table 1). The CEP 7, CEP 9, and CEP 17 probes were included to determine allelic gain or loss of the corresponding LSI probes on those chromosomes (e.g., 9p21 on chromosome 9) or aneusomy of those chromosomes.

TABLE 1

FISH Probes and Gene Target Locations Used for Probe Selection

| Probe Set | Red | Green | Aqua | Gold |
|---|---|---|---|---|
| I | LSI 9p21 (P16) | LSI 5p15 | CEP 9 | LSI 5q21-22 (APC) |

TABLE 1-continued

FISH Probes and Gene Target Locations Used for Probe Selection

| Probe Set | Red | Green | Aqua | Gold |
|---|---|---|---|---|
| II | CEP Y | LSI 17q11.2-12 (HER2/NEU) | CEP 17 | LSI 17p13.1 (P53) |
| III | LSI 20q13.2 | LSI 8q24.12-13 (C-MYC) | CEP 7 | LSI 7p12 (EGFR) |

With the exception of the LSI® 5q21-22 (APC) probe, the LSI® and CEP® probes are commercially available from Vysis, Inc. (Downers Grove, Ill., www.vysis.com) labeled with SpectrumOrange™. Instead of the SpectrumOrange™ label, the nucleic acid starting material was transaminated and then chemically labeled using TEXAS RED (red), 6-[fluorescein 5-(and-6)-carboxamido]hexanoic acid (green), 7-diethylaminocoumarin-3-carboxylic acid (aqua) and 5-(and 6-)-carboxyrhodamine 6G (gold). The transamination and labeling process is described in Bittner, et al., U.S. Pat. No. 5,491,224, incorporated herein by reference.

The LSI® 5q21-22 (APC) probe was made from two BAC clones (Identification Nos. RPCI11-60p20 and RPCI11-141i11 obtained from Invitrogen). The size of the contig was about 246 kb and the APC gene was located in about the center of the contig. The probe was transaminated and labeled as above.

Study Population

Institutional review board (IRB) approval was obtained for this study and informed consent was obtained from all enrolled patients. The study included 174 patients seen at the Mayo Clinic, Rochester, from 2002 till 2003. Patients were enrolled in the study if they had previously identified, pathology-proven BE or pathology proven BE at the time of entry into the study. Seventeen females and 153 males ranging in age from 31 to 87 were studied.

Specimen and Pathology Findings

Cytologic brushing specimens were obtained by sweeping a gastrointestinal sheath brush (Hobbs Medical Inc., Stafford Springs, Conn.) over the surface of the suspected area of IM, BE associated neoplasia, or the location of previously diagnosed BE after initially eliminating the mucus layer with a spray of n-acetyl-cysteine. The brush was immediately placed in a bottle containing PreservCyt® Solution (Cytyc Corporation, Boxborough, Mass.) and delivered to the FISH laboratory for processing.

The pathologic findings for endoscopic brushing specimens that contained a sufficient number of cells for enumeration, greater than 50 cells for at least one of the three probe sets could be enumerated in 170 of the 174 specimens, were as follows: normal (N=34), IM (N=28), LGD (N=24), HGD (N=67), and EA (N=17). Specimens that had more than one pathology result at the time of the brushing, due to multiple biopsies or endomucosal resection (EMR), were categorized according to the most advanced of the histologic categories observed (e.g., if a patient had two biopsies, one was IM and the other was HGD, the specimen would be placed into the HGD classification).

Isolation of Cells for FISH Analysis

Specimens were processed within 72 hours of collection. Cells were removed from the brush by washing the brush with 10 ml of 3:1 methanol: glacial acetic acid fixative solution four times and transferring the mixture to a 50 ml conical centrifuge tube. Cells were then pelleted by centrifugation at 800×g for eight minutes. The supernatant was removed and the cell pellet was resuspended in 10 ml of 3:1 methanol: acetic acid solution. The cell suspension was then centrifuged at 300×g for eight minutes. Depending on the size of the cell pellet, all but approximately 50-150 µl of the supernatant was then removed. The cell pellet was then resuspended by gentle vortexing and stored at −4° C. for further use.

Preparation of Slides for FISH Analysis

A portion of the cell suspension (usually about 10-50 µl) was dropped onto three wells (a well for each of the three probe sets) with a micropipettor. The cellularity (i.e., the density of the cells in the well) was assessed with a phase contrast microscope. If the cellularity was too low, additional portions of the cell pellet were added to the well until the desired cellularity (i.e., the greatest number of cells per spot with minimal cell overlap) was reached or the cell pellet was exhausted.

FISH Hybridization

FISH was performed in the following fashion: slides were incubated in 2× standard saline citrate (SSC) at 37° C. for 13 minutes, 0.05 mg/ml pepsin in 10 mM HCl at 37° C. for 14 minutes, phosphate buffered saline (PBS) at room temperature (RT) for five minutes, 1% formaldehyde at RT for five minutes and PBS at RT for five minutes. Slides were then placed in RT 70%, 85%, and 100% ethanol solutions for two minutes each and allowed to air-dry. Following this pre-treatment, 5 µl (1.5 µl probe, 3.5 µl LSI/WCP hybridization buffer) of the appropriate probe mixture was applied to the designated area. The slides were then coverslipped, edges of the coverslip sealed with rubber cement, and placed in a Vysis HYBrite™ Denaturation/Hybridization System where the probe and target DNA were co-denatured at 73° C. for three minutes and then incubated at 37° C. for about 15 hours. Following the overnight hybridization, slides were washed in 2×SSC/0.1% NP-40 at 73° C. for 40 seconds and rinsed in 2×SSC/0.1% NP-40 at room temperature for several minutes. Ten µl of DAPI I counterstain was then applied to each hybridized area and the slides were then coverslipped.

Enumeration of FISH Signals

Slides were analyzed with an epi-fluorescence microscope equipped with single band-pass filters for the DAPI counterstain, Spectrum Aqua®, and Spectrum Gold®, along with a dual-pass filter for FITC/Texas Red. FISH signal enumeration was performed without knowledge of the patient's clinical or histologic findings. The specimen was analyzed by counting and recording the number of signals for each probe in 50-100 consecutive non-inflammatory, non-squamous cells. Squamous cells were enumerated only for the occasional case in which no other cell type was present. Care was taken not to score overlapping cells. One hundred cells were enumerated per hybridization when possible. Enumeration of at least 50 cells was required for the case to be included in the data analysis.

Analysis of Enumeration Data

Each of the 50-100 cells analyzed per specimen was classified with respect to the 11 loci on autosomes as having the normal complement of the locus (two FISH signals), gain of the locus (greater than two FISH signals), or loss of the locus (less than two FISH signals). For CEP Y, one copy of the centromeric sequence was normal, 2 or more signals indicated gain, and zero signals indicated loss. For multiple loci on the same chromosome (e.g., CEP 17, 17p13.1, and 17q11.2-12) relative gain or loss of one locus with respect to the other was also recorded for each cell. Relative gain of one locus was indicated by a ratio of the FISH signals on that locus to the FISH signals of a second locus being greater than one. The ratio was less than one for relative loss. The percentages of cells with gain and loss were tabulated for each locus in each specimen and the means (x) and standard deviations (s) of the cell percentages were calculated for each diagnostic group (normal, IM, LGD, HGD, EA; see Tables 2 and 3), excluding specimens of insufficient signal quality for enumeration.

TABLE 2

Mean and Standard Deviation of the Percentages of Cells with Gain or Loss in Normal Specimens.

| | | Normal Specimen Set | | | |
|---|---|---|---|---|---|
| PROBE | N | Mean Percent of Cells with Gain | SD - Percent Cells with Gain | Mean Percent of Cells with Loss | SD - Percent of Cells with Loss |
| 5p15 | 33 | 0.21 | 0.42 | 1.93 | 1.93 |
| 5q21-22 | 33 | 0.35 | 0.56 | 2.31 | 3.27 |
| CEP 7 | 31 | 0.45 | 0.72 | 2.06 | 1.21 |
| 7p12 | 31 | 0.57 | 0.74 | 1.81 | 1.64 |
| 8q24.12-13 | 31 | 0.48 | 0.72 | 1.81 | 1.18 |
| CEP 9 | 33 | 0.18 | 0.46 | 2.67 | 2.05 |
| 9p21 | 33 | 0.61 | 0.86 | 3.53 | 3.13 |
| CEP 17 | 32 | 0.16 | 0.51 | 5.13 | 2.93 |
| 17p13.1 | 32 | 0.64 | 1.13 | 4.72 | 3.01 |
| 17q11.2-12 | 32 | 0.84 | 1.32 | 3.88 | 2.43 |
| 20q13 | 31 | 0.74 | 1.21 | 1.68 | 1.49 |
| CEP Y | 28 | 0.36 | 0.74 | 1.90 | 3.19 |
| 5p15/5q21-22 | 33 | 2.10 | 3.03 | 1.86 | 1.79 |
| 7p12/CEP 7 | 31 | 1.95 | 1.23 | 1.55 | 1.65 |
| 9p21/CEP 9 | 33 | 2.97 | 2.12 | 3.38 | 3.15 |
| 17p13.1/CEP 17 | 32 | 4.30 | 2.37 | 3.38 | 2.09 |
| 17q11.2-12/CEP17 | 32 | 5.30 | 2.81 | 3.39 | 2.44 |
| 17q11.2-12/17p13.1 | 32 | 4.63 | 3.19 | 3.68 | 2.42 |

The discriminate value (DV), defined as $(x_1-x_2)^2/(s_1^2+s_2^2)$, where $x_1$ and $s_1$ refer to one of the IM, dysplasia, or cancer groups, and $x_2$ and $s_2$ refer to the group of normal specimens, was used as a measure of the ability of gain or loss of a locus to distinguish between a sample from the group of patients having either LGD, HGD, or EA and a sample from the group of patients not exhibiting one of these abnormalities (i.e., IM and normal group of patients). Larger DV values are indicative of a greater ability to distinguish between the two groups of patients. As another measure of discrimination, the Student's t-test was applied to the percentages of abnormal cells of two different specimen groups to determine if the differences were statistically significant (probabilities <0.05 were considered significant).

Sensitivities and specificities were calculated by applying cutoffs to the percentages of cells exhibiting gains or losses for each of the 12 loci. A specimen was considered positive for gain or loss of a locus if the percentage of cells with the respective gain or loss exceeded the cutoff for that locus. The sensitivity for detecting specimens with a particular diagnosis was equal to the fraction of specimens in that group that were positive. Specimens that did not provide at least 50 cells with FISH signals of sufficient quality for counting were excluded from the calculation. Specificity relative to a control group was calculated as one minus the fraction of the control group specimens that were positive using the same criteria (false positives). For combinations of probes, cutoffs were applied to each targeted locus independently. If any of the loci targeted by the probe combination were positive for the respective cutoff, then the specimen was considered positive. The parameter 'distance from ideal' (DFI), which incorporates both sensitivity and specificity, was used to assess the relative performance of each probe or combination of probes. DFI is defined as $[(1-\text{sensitivity})^2+(1-\text{specificity})^2]^{1/2}$. DFI is 0 for an assay with performance of 100% sensitivity and 100% specificity and increases to 1.414 for an assay with 0% specificity and 0% sensitivity.

Probe complementation was evaluated by calculating sensitivity, specificity, and DFI values for all possible probe combinations up to combinations of four probes, over a wide range of cut-off values. Only probes providing p-values less than 0.05 in the discrimination analysis (Table 4) were utilized in these calculations in order to reduce the likelihood that low DFI values would result from the combination of random events, and to reduce the computation time. Cut-off values between 0 and 100% abnormal cells at 1% increments were calculated for each single probe. Since each probe in a combination may have a different optimal cut-off value, cut-off values were varied independently for each probe in a particular combination. Independent variation of cutoff values between 0 and 100% and 1% increments cells was not practical for probe combinations, so cutoffs based on the standard deviations of the average percentage of abnormal cells in for each locus and each diagnostic group were calculated first. Cut-offs were generated as x+n*s, where x and s are the mean and standard deviation for a particular locus in the control specimens group (x and s for LGD were used for discriminating EA+HGD, and x and s for IM were used for discriminating LGD), and n is a multiplier typically ranging from −1 to 5 in increments of 0.2. For probe combinations the cut-off was calculated using x and s for each probe in the combination individually, but using the same value of n. This procedure provided cut-off values adjusted to each probe based on the level of abnormality and extent of variation in the control group. To a first approximation, basing cut-offs on x and common multiples of s establishes a similar specificity relative to the control group for each probe in the combination for a particular set of cut-offs (assuming a normal distribution of the percentage of abnormal cells within the control group). Probes and probe combinations at each cut-off or set of cut-off values were sorted from lowest to highest DFI in order to identify the better performers. Optimal cut-off values for top performing probe combinations (lowest DFI values) were further refined by independently varying cut-offs in 1% abnormal cell increments flanking the optimal cutoffs established using x and s of the control specimen group.

Receiver Operator Characteristics (ROC) graphs were generated by plotting sensitivity versus 1—specificity for a particular probe or probe combination over the range of cutoff values examined (see above). Since independently varied cut-off values in probe combinations generates multiple sensitivity values for each specificity value, only the highest sensitivity value at each specificity value was plotted, representing the optimal combination of cut-off values for each specificity. Relative performance of a probe or combination of probes could be assessed from these curves by the areas under the curves (better performance indicated by larger areas) or by the distance of closest approach to the point (0, 1) on the graph (100% specificity, 100% sensitivity). Notice that the distance of any point on the curves to the point (0, 1) is equal to the DFI value, and probe combinations with lower DFI values perform better than those with higher DFI values. The cell cutoffs associated with lowest DFI values can then be used as the basis for setting optimal assay cutoffs though points on the ROC curve with somewhat lower DFI values may be chosen, after considering the relative clinical importance of sensitivity and specificity. For example, a point on the curve with a slightly higher sensitivity but lower specificity might be chosen over another point on the curve that has a lower sensitivity and higher specificity, depending upon medical need.

Results
Discrimination Analysis

The ability of each FISH probe to discriminate between the group of patients having LGD, HGD, and EA and patients not having these abnormalities (i.e., patients with "normal" or IM diagnosis) was initially examined by comparing the frequency of abnormal (nondisomic) cells within each histologic category. Table 2 lists the number of specimens evaluated (N), the mean percent of cells with gain or loss, and the standard deviation of the percentage of cells with gain or loss for each locus and locus ratio within the normal specimen group. Means and standard deviations were calculated for each of the histologic categories, but for brevity, only the values for HGD are listed in Table 3. Table 3 also lists DV's and p-values, quantities that reflect the ability of particular probes or probe ratios to differentiate between HGD and normal specimens. DV's and p-values for all of the histologic groups compared to the normal specimen group and are listed in Table 4. The DV's and p-values were consistent in that lower p-values were accompanied by higher DV's. Entries of NA in Table 4 for DV and p-values indicate that the mean of the diagnostic group was lower than that of the normal group.

TABLE 3

Mean percent of cells, Standard Deviation, Discriminate Value and p Value of Probes for Gain or Loss in HGD Specimens.

| | | HGD Specimen Set | | | | | | | |
|---|---|---|---|---|---|---|---|---|---|
| PROBE | N | Mean Percent of Cells with Gain | SD - Percent Cells with Gain | DV - Gain | p Value - Gain | Mean Percent of Cells with Loss | SD - Percent of Cells with Loss | DV - Loss | p Value - Loss |
| 5p15 | 66 | 9.69 | 21.26 | 0.20 | <0.01 | 5.52 | 10.91 | 0.11 | 0.01 |
| 5q21-22 | 66 | 5.45 | 11.46 | 0.20 | <0.01 | 5.27 | 10.29 | 0.08 | 0.04 |
| CEP 7 | 67 | 17.08 | 26.03 | 0.41 | <0.01 | 2.27 | 1.84 | 0.01 | 0.49 |
| 7p12 | 67 | 17.40 | 25.85 | 0.42 | <0.01 | 1.99 | 2.30 | <0.01 | 0.65 |
| 8q24.12-13 | 67 | 21.64 | 27.44 | 0.59 | <0.01 | 1.63 | 1.65 | 0.01 | 0.54 |
| CEP 9 | 66 | 7.79 | 15.34 | 0.25 | <0.01 | 4.33 | 8.44 | 0.04 | 0.13 |
| 9p21 | 66 | 1.95 | 3.48 | 0.14 | <0.01 | 27.20 | 30.26 | 0.61 | <0.01 |
| CEP 17 | 67 | 9.85 | 19.29 | 0.25 | <0.01 | 5.72 | 4.33 | 0.01 | 0.43 |
| 17p13.1 | 67 | 1.56 | 2.34 | 0.13 | 0.01 | 12.82 | 16.46 | 0.23 | <0.01 |
| 17q11.2-12 | 67 | 14.99 | 23.88 | 0.35 | <0.01 | 3.08 | 3.27 | 0.04 | 0.17 |
| 20q13 | 67 | 18.18 | 24.84 | 0.49 | <0.01 | 1.85 | 1.82 | 0.01 | 0.62 |
| CEP Y | 62 | 2.03 | 10.45 | 0.03 | 0.22 | 27.39 | 31.64 | 0.64 | <0.01 |
| 5p15/5q21-22 | 66 | 9.82 | 19.58 | 0.15 | <0.01 | 4.90 | 10.64 | 0.08 | 0.03 |
| 7p12/CEP 7 | 67 | 3.68 | 3.92 | 0.18 | <0.01 | 2.86 | 4.79 | 0.07 | 0.05 |
| 9p21/CEP 9 | 66 | 2.08 | 2.28 | 0.08 | 0.06 | 26.69 | 30.16 | 0.59 | <0.01 |
| 17p13.1/CEP 17 | 67 | 4.06 | 2.91 | <0.01 | 0.67 | 18.95 | 23.81 | 0.42 | <0.01 |
| 17q11.2-12/CEP17 | 67 | 11.99 | 15.53 | 0.18 | <0.01 | 3.86 | 3.63 | 0.01 | 0.45 |
| 17q11.2-12/17p13.1 | 67 | 24.15 | 26.80 | 0.52 | <0.01 | 2.41 | 1.84 | 0.18 | 0.01 |

TABLE 4

Discriminate Value and p Value of Gain and Loss per Histologic Specimen Type.

| | IM Specimens | | | | LGD Specimens | | | | HGD Specimens | | | | EA Specimens | | | |
|---|---|---|---|---|---|---|---|---|---|---|---|---|---|---|---|---|
| PROBE | DV, gain | p, gain | DV, loss | p, gain | DV, gain | p, gain | DV, loss | p, loss | DV, gain | p, gain | DV, loss | p, loss | DV, gain | p, gain | DV, loss | p, loss |
| 5p15 | 0.12 | 0.08 | <0.01 | 0.94 | 0.27 | 0.02 | <0.01 | 0.74 | 0.20 | <0.01 | 0.11 | 0.01 | 0.45 | 0.02 | 0.08 | 0.26 |
| 5q21-22 | 0.03 | 0.35 | N/A | N/A | 0.07 | 0.20 | N/A | N/A | 0.20 | <0.01 | 0.08 | 0.04 | 0.43 | 0.02 | 0.31 | 0.03 |
| CEP 7 | 0.23 | 0.02 | <0.01 | 0.62 | 0.08 | 0.19 | 0.05 | 0.25 | 0.41 | <0.01 | <0.01 | 0.49 | 0.52 | 0.01 | 0.03 | 0.44 |
| 7p12 | 0.12 | 0.08 | 0.04 | 0.31 | 0.08 | 0.19 | 0.04 | 0.31 | 0.42 | <0.01 | <0.01 | 0.65 | 0.70 | <0.01 | N/A | N/A |
| 8q24.12-13 | 0.11 | 0.08 | 0.12 | 0.07 | 0.09 | 0.16 | 0.02 | 0.50 | 0.59 | <0.01 | N/A | N/A | 0.54 | <0.01 | 0.06 | 0.29 |
| CEP 9 | 0.06 | 0.20 | N/A | N/A | 0.09 | 0.16 | N/A | N/A | 0.25 | <0.01 | 0.04 | 0.13 | 0.49 | 0.01 | N/A | N/A |
| 9p21 | <0.01 | 1.00 | 0.15 | 0.05 | 0.05 | 0.26 | 0.49 | <0.01 | 0.14 | <0.01 | 0.61 | <0.01 | 0.28 | 0.05 | 0.51 | 0.01 |
| CEP 17 | 0.17 | 0.05 | 0.02 | 0.45 | 0.06 | 0.24 | 0.04 | 0.31 | 0.25 | <0.01 | 0.01 | 0.43 | 0.72 | <0.01 | N/A | N/A |
| 17p13.1 | <0.01 | 0.96 | 0.06 | 0.22 | <0.01 | 0.71 | 0.06 | 0.25 | 0.13 | <0.01 | 0.23 | <0.01 | 0.26 | 0.06 | 0.15 | 0.14 |
| 17q11.2-12 | N/A | N/A | <0.01 | 0.75 | 0.06 | 0.26 | N/A | N/A | 0.35 | <0.01 | N/A | N/A | 0.69 | <0.01 | N/A | N/A |
| 20q13 | 0.10 | 0.10 | 0.09 | 0.12 | 0.09 | 0.17 | <0.01 | 0.89 | 0.49 | <0.01 | <0.01 | 0.62 | 0.54 | <0.01 | N/A | N/A |
| CEP Y | 0.04 | 0.33 | 0.05 | 0.28 | N/A | N/A | 0.19 | 0.08 | 0.03 | 0.22 | 0.64 | <0.01 | 0.06 | 0.35 | 0.83 | <0.01 |
| 5p/5q | <0.01 | 0.98 | N/A | N/A | N/A | N/A | 0.04 | 0.32 | 0.15 | <0.01 | 0.08 | 0.03 | 0.41 | 0.02 | 0.04 | 0.44 |
| 7p/CEP7 | 0.03 | 0.41 | <0.01 | 0.79 | 0.01 | 0.57 | N/A | N/A | 0.18 | <0.01 | 0.07 | 0.05 | 0.25 | 0.07 | N/A | N/A |
| 9p/CEP9 | N/A | N/A | 0.15 | 0.05 | N/A | N/A | 0.48 | <0.01 | N/A | N/A | 0.59 | <0.01 | N/A | N/A | 0.60 | <0.01 |
| 17p/CEP17 | 0.01 | 0.58 | 0.09 | 0.14 | 0.02 | 0.47 | 0.13 | 0.09 | N/A | N/A | 0.42 | <0.01 | N/A | N/A | 0.51 | 0.01 |
| 17q/CEP17 | 0.02 | 0.51 | 0.04 | 0.31 | 0.10 | 0.13 | <0.01 | 0.62 | 0.18 | <0.01 | 0.01 | 0.45 | 0.40 | 0.02 | N/A | N/A |
| 17q/17q | 0.06 | 0.24 | <0.01 | 0.74 | 0.11 | 0.12 | N/A | N/A | 0.52 | <0.01 | N/A | N/A | 0.54 | <0.01 | N/A | N/A |

The p-values listed in Table 4 indicate that gains of chromosomes 7 and 17 centromeres occur in a significantly higher percentage of cells in IM specimens than in normal specimens. In addition, loss of the 9p21 locus occurs in a significantly higher percentage of cells for IM specimens than for normal specimens. For LGD specimens, loss of the 9p21 locus, measured either by the number signals per cell or by ratio to the number of CEP 9 signals, was significant. Lower p-values and higher DV's for the LGD specimens as compared to IM specimens indicate that loss of the 9p21 locus can better distinguish LGD specimens than IM specimens from the normal specimens. Gain of the 5p15 locus was significantly more common in the LGD specimen group than the normal specimen group.

The number of abnormal loci was considerably greater for HGD specimens than either IM or LGD specimens (Tables 3 and 4), with all individual loci and ratios of loci showing significantly elevated gains relative to the normal group, except for CEP Y and the ratios of 9p21/CEP 9 and 17p13.1/CEP 17. Significantly higher levels of loss were evident for 5p15, 5q21-22, 9p21, 17p13.1, CEP Y, 5p15/5q21-22, 7p12/CEP 7, 9p21/CEP 9, and 17p13.1/CEP 17.

Similar to HGD specimens, many EA specimens (Table 4) showed significantly increased percentages of cells with gain relative to normal specimens, including all loci and loci ratios tested except 17p13.1, CEP Y, 7p12/CEP 7, 9p21/CEP 9, and 17p13.1/CEP 17. Significantly increased percentages of cells with loss were found for 5q21-22, 9p21, CEP Y, 9p21/CEP 9, and 17p13.1/CEP 17.

Abnormality Versus Histological Progression

Figure 1B:
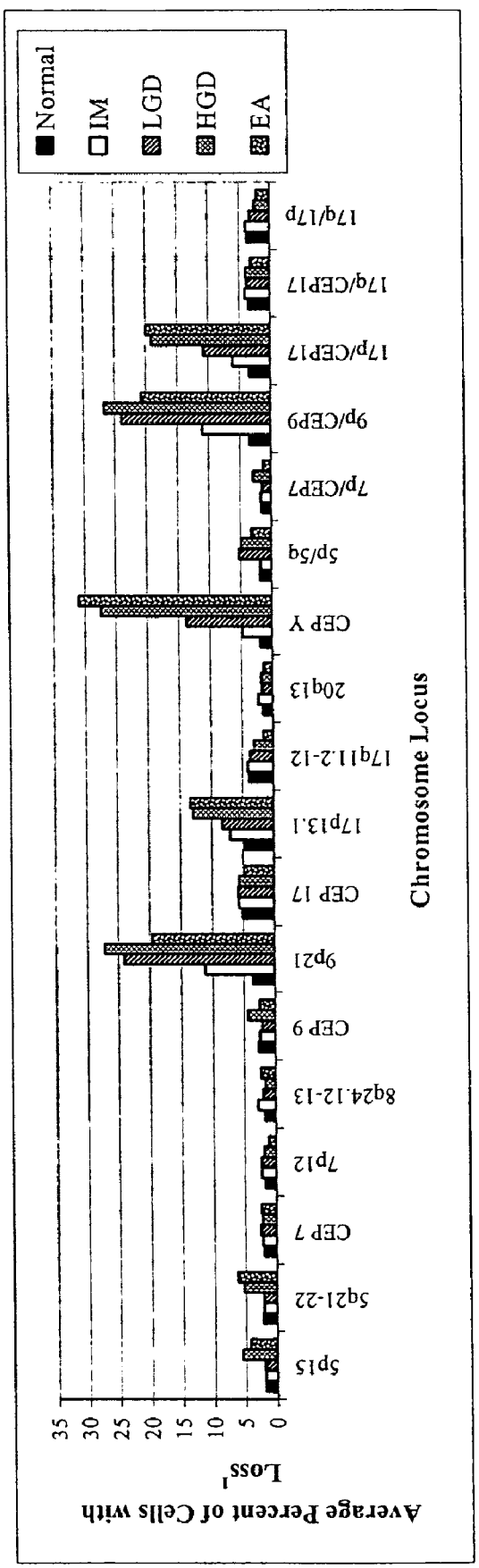

FIGS. 1A and 1B show the average percentage of cells exhibiting gains or loss, respectively at each locus or loci ratio for each histologic category. For a particular locus or loci ratio, the average percentages of cells with locus gain usually increased with progression from normal to EA, with the maximum increases occurring at the LGD to HGD and HGD to EA transitions. The only clear deviations from this trend were gain of CEP Y and the ratios 9p/CEP 9 and 17p/CEP 17. The greatest increase in the number of cells showing gain of CEP Y occurred at the normal to IM transition while the level of gain was fairly insensitive to histologic stage for the 9p/CEP 9 and 17p/CEP 17 ratios.

The most marked increase in the percentages of cells with locus gain generally occurred at the LGD to HGD transition. This was true for 5p15, CEP 7, 7p12, 8q24, CEP 9, CEP 17,17q, 20q, 5p/5q, and 17q/17p. For 9p21, 17p, 7p/CEP 7, and 17q/CEP 17 the sharpest increase in percent of cells exhibiting gain came with progression from HGD to EA, while CEP Y was the only locus showing the greatest increase at the normal to IM transition.

Only 9p21, 17p, CEP Y, 9p/CEP 9, and 17p/CEP 17 showed clearly increasing levels of loss with progression from normal to EA histological category. For 9p21 and its ratio to CEP 9 the sharpest increase in percentage cells showing these abnormalities was observed at the IM to LGD transition, while for 17p, 17p/CEP 17, and CEP Y the sharpest increase was at the LGD to HGD transition.

Single Probe Sensitivities, Specificities, and DFI Values

Sensitivities, specificities, and DFI values were calculated for individual probes over a range of cutoff values. For the combined EA and HGD groups versus the normal through LGD groups, the best DFI values (i.e. lowest DFI values) were obtained for loss of CEP Y and gain of 8q24.12-13, 17q11.2-12, CEP 17, 7p12, and 20q13. Of these probes, loss of CEP Y and gain of 8q24.12-13, 7p12, and 20q13 were consistently identified by the different methods of assessing single probe performance as it relates to the LGD-to-HGD transition. In addition, gain of 17q11.2-12, 17q11.2-12/CEP 17, and 17q11.2-12/17p12 all ranked highly by the different analysis methods.

Similar analysis for the LGD group versus the combined normal and IM groups revealed, the best DFI values (i.e., lowest DFI values) for 9p21, 9p21/CEP 9, 5p15, CEP Y, and CEP 17, as well as gain of 8q24.12-13 and 20q13. Of these probes, 9p21 and 9p21/CEP 9, and to a lesser extent 5p15, were consistently identified by the different methods of assessing single probe performance as it relates to the IM-to-LGD transition.

Complementation Analysis

In order to determine which probes work best in combination, complementation analysis was performed. Sensitivities, specificities, and DFI values were calculated for all possible probe combinations for each of the diagnostic categories. Combinations of up to 4 probes were analyzed, since four probes are easily combined into a multicolor probe set suitable for viewing through the microscope (visible light emitting labels). In the initial analysis, cutoff values were generated as the mean plus multiples (n) of the standard deviations of the percentages of cells with gain or loss of the less abnormal of the two specimen groups being compared (e.g., normal+IM specimens when being compared to LGD specimens). Table 5A lists the top performing combinations of 4 probes based on DFI of the adenocarcinoma+HGD groups relative to the normal+IM+LGD groups with the relevant values of n, DFI, sensitivity and specificity. Table 6A lists the top performing combinations of 4 probes based on DFI of the LGD group versus the normal+IM groups. Tables 5C and 6C list four-probe combinations and their respective DFI values for LGD vs. norm+IM (meta), HGD vs. norm+IM+LGD, EA vs. norm+IM+LGD+HGD, and EA+HGD vs. norm+IM+LGD.

For many of the top performing probe combinations listed in Tables 5A and 6A, all of which are probe combinations of the invention, the optimal cutoff values were further refined by independently varying the cutoffs in 1% abnormal cell increments for each probe in each combination over a small range (e.g., 10-20%) about cutoffs based on the n values in Tables 5A and 6A. The refined optimal cutoffs and DFI values for this process are listed in Tables 5B and 6B.

Receiver Operator Curves

Figure 2:
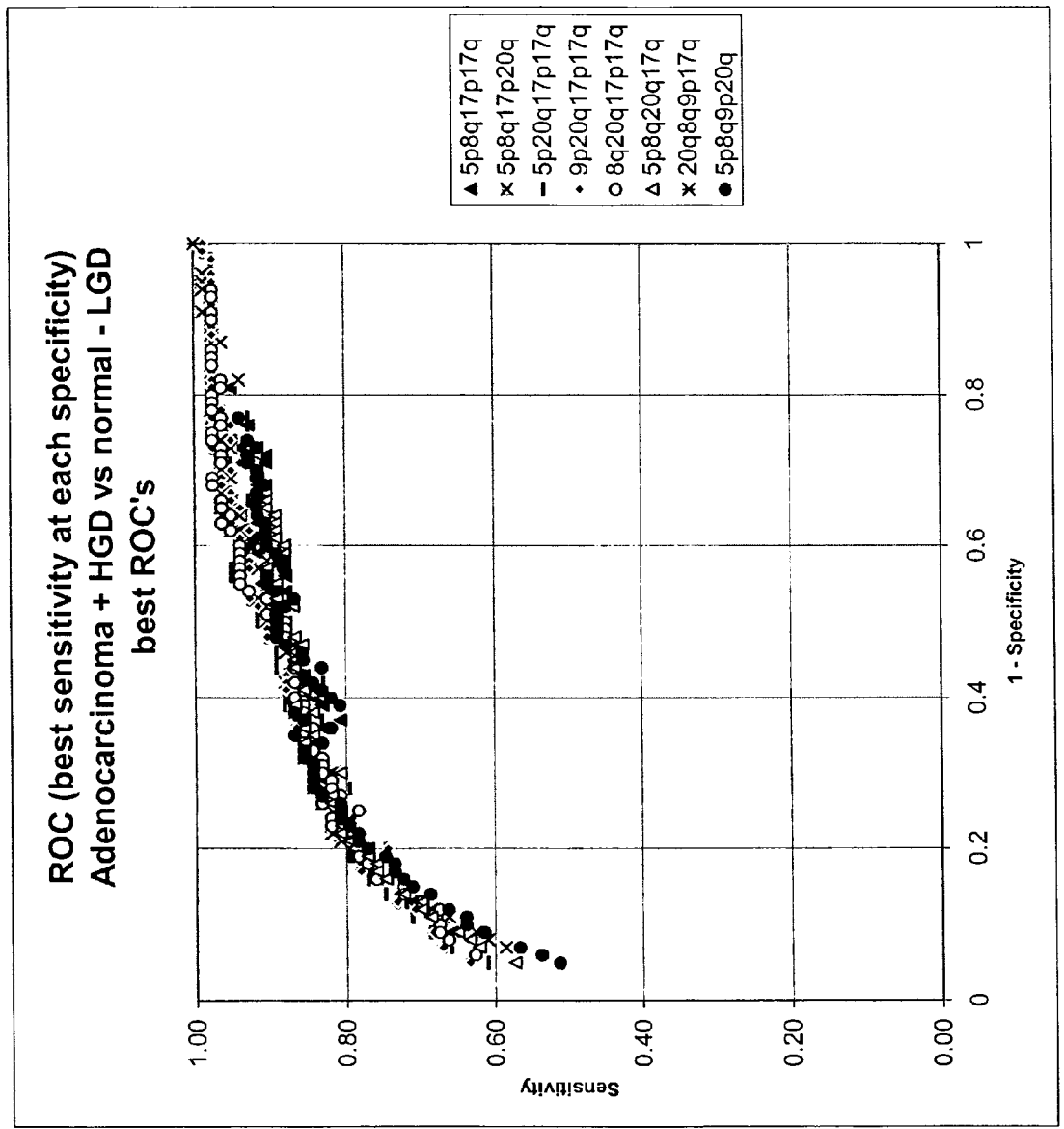
FIG. 2 shows ROC curves that illustrate the relationships between sensitivity and specificity for detecting EA plus HGD specimens relative to the collective group of normal, IM, and LGD specimens for different possible four probe combinations.

ROC plots were generated using a number of four-probe combinations selected from the complementation analysis. The ROC curves for a few of the better performing four-probe combinations, as judged by lower DFI values, are plotted in FIGS. 2 and 3. ROC curves in FIG. 2 illustrate the relationships between sensitivity and specificity for detecting EA plus HGD specimens relative to the collective group of normal, IM, and LGD specimens. The region of each of these curves that most closely approaches the ideal point of (0, 1) occurs near values of equal sensitivity and specificity. Points on these curves at which sensitivity and specificity are equal range from about 77% to 80% (DFI=0.32 to 0.28). Therefore, on a functional basis the best performing probe combinations can be considered to be those combinations of probes that can provide DFI values less than 0.33. However, probe combinations with DFI values >0.33 may still be of value. It is estimated that the sensitivity and specificity of current endoscopy with biopsy are about 70% for discriminating EA+HGD from normal+IM+LGD. This corresponds to a DFI value of 0.42. Therefore, probe combinations that provide DFI values less than 0.42 would provide a performance improvement over existing methodology, while at the same time providing simpler and faster sampling during endoscopy. Probes found to be useful in various combinations to detect EA plus HGD versus normal through LGD include 5p15, 8q24.12-13, 7p12, 5q21-22, 9p21, CEP 17, 17p13.1, 17q11.2-12, and 20q13.2 (gain at each locus).

Figure 3:
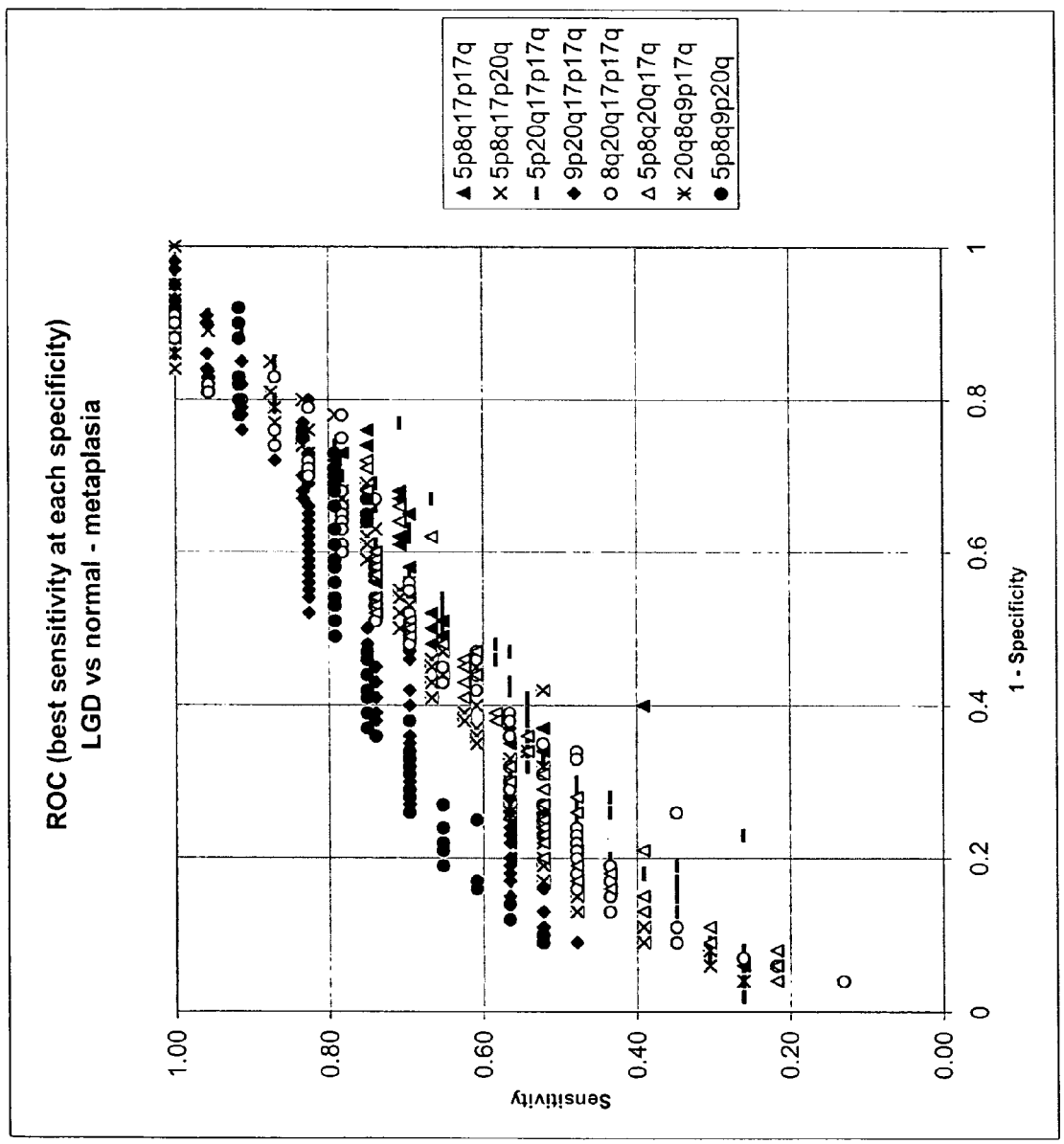
FIG. 3 shows ROC curves that illustrate the relationships between sensitivity and specificity for detecting LDG specimens relative to normal+IM specimens for different possible probe combinations.

The ROC curves shown in FIG. 3 illustrate the relationships between sensitivity and specificity for detecting LDG specimens relative to normal+IM specimens. Points of equal sensitivity and specificity range from about 55% to 70% (DFI=0.64 to 0.42). Therefore, operationally, probe combinations providing DFI values less than 0.64 can be considered to be the better performers. Probe combinations that performed well in detecting EA+HGD and also showed the best utility in detecting LGD versus normal+IM included 9p21 in the probe combination. Note that to provide the optimal sensitivity for detecting EA plus HGD, gain of 9p21 was used in calculations of sensitivity and specificity, while loss of 9p21 was optimal for detecting LGD.

TABLE 5A

Cutoffs based on means (x) and multiples (n) of standard deviations (s) of the LGD specimen group and resulting performance characteristics of 4-probe combinations for discriminating the combined group of EA + HGD specimens from the combined group of normal, IM, and LGD specimens.

| | | | | C/O | IM | | LGD | | HGD | | EA | | EA + HGD | | spec vs norm | DFI vs norm | spec vs norm-LGD | DFI vs norm-LGD |
|---|---|---|---|---|---|---|---|---|---|---|---|---|---|---|---|---|---|---|
| Probe 1 | Probe 2 | Probe 3 | Probe 4 | n | N | sens | N | sens | N | sens | N | sens | N | sens | norm | norm | LGD | LGD |
| 20q gain | CEP 9 gain | 7p gain | 5q gain | -0.2 | 28 | 0.29 | 23 | 0.30 | 67 | 0.81 | 16 | 0.94 | 83 | 0.83 | 0.90 | 0.20 | 0.78 | 0.28 |
| 17p loss | 17q gain | CEP 9 gain | 5p gain | 0.0 | 26 | 0.15 | 23 | 0.30 | 67 | 0.72 | 16 | 0.94 | 83 | 0.76 | 0.94 | 0.25 | 0.84 | 0.29 |
| 17p loss | 20q gain | 17q gain | 5p gain | 0.0 | 26 | 0.19 | 23 | 0.30 | 67 | 0.73 | 16 | 0.94 | 83 | 0.77 | 0.93 | 0.24 | 0.82 | 0.29 |
| CEP 9 gain | 8q gain | 7p gain | 5q gain | -0.2 | 28 | 0.29 | 23 | 0.43 | 67 | 0.81 | 16 | 0.94 | 83 | 0.83 | 0.93 | 0.18 | 0.75 | 0.30 |
| CEP 9 gain | 7p gain | 5q gain | 5p gain | -0.2 | 28 | 0.29 | 23 | 0.35 | 67 | 0.76 | 17 | 0.88 | 84 | 0.79 | 0.97 | 0.22 | 0.79 | 0.30 |
| 17p loss | 17q gain | 5q gain | 5p gain | 0.0 | 26 | 0.15 | 23 | 0.30 | 67 | 0.70 | 16 | 0.94 | 83 | 0.75 | 0.94 | 0.26 | 0.84 | 0.30 |
| 17p loss | 20q gain | 17q gain | 9p gain | 0.2 | 25 | 0.08 | 23 | 0.30 | 67 | 0.70 | 15 | 0.93 | 82 | 0.74 | 0.86 | 0.29 | 0.83 | 0.31 |
| 17p loss | 17q gain | CEP 17 gain | 5p gain | 0.0 | 26 | 0.19 | 23 | 0.35 | 67 | 0.70 | 16 | 0.94 | 83 | 0.75 | 0.97 | 0.26 | 0.82 | 0.31 |
| 17p loss | 17q gain | 8q gain | 5p gain | 0.0 | 26 | 0.27 | 23 | 0.30 | 67 | 0.73 | 16 | 0.94 | 83 | 0.77 | 0.93 | 0.24 | 0.79 | 0.31 |
| 17p loss | 17q gain | 7p gain | 5p gain | 0.0 | 26 | 0.23 | 23 | 0.30 | 67 | 0.72 | 16 | 0.94 | 83 | 0.76 | 0.93 | 0.25 | 0.81 | 0.31 |
| 17p loss | 17q gain | CEP 7 gain | 5p gain | 0.0 | 26 | 0.23 | 23 | 0.30 | 67 | 0.72 | 16 | 0.94 | 83 | 0.76 | 0.93 | 0.25 | 0.81 | 0.31 |
| 20q gain | 17q gain | 8q gain | 5p gain | 0.0 | 26 | 0.27 | 23 | 0.30 | 67 | 0.72 | 16 | 0.94 | 83 | 0.76 | 0.96 | 0.24 | 0.81 | 0.31 |
| 20q gain | 17q gain | 9p gain | 8q gain | 0.0 | 25 | 0.20 | 23 | 0.26 | 67 | 0.73 | 15 | 0.93 | 82 | 0.77 | 0.83 | 0.29 | 0.79 | 0.31 |
| 17p loss | 20q gain | 17q gain | 9p gain | 0.0 | 25 | 0.16 | 23 | 0.30 | 67 | 0.75 | 15 | 0.93 | 82 | 0.78 | 0.79 | 0.30 | 0.78 | 0.31 |
| 20q gain | 17q gain | 7p gain | 5p gain | 0.0 | 26 | 0.23 | 23 | 0.30 | 67 | 0.70 | 16 | 0.94 | 83 | 0.75 | 0.96 | 0.26 | 0.82 | 0.31 |
| 20q gain | 17q gain | CEP 7 gain | 5p gain | 0.0 | 26 | 0.23 | 23 | 0.30 | 67 | 0.70 | 16 | 0.94 | 83 | 0.75 | 0.96 | 0.26 | 0.82 | 0.31 |

TABLE 5B

Refined cutoffs and performance characteristics of 4-probe combinations for discriminating the combined group of EA and HGD specimens from the combined group of normal, IM, and LGD specimens.

| Probes | | | | Percent Cell Cutoffs | | | | Performance | | |
|---|---|---|---|---|---|---|---|---|---|---|
| 1 | 2 | 3 | 4 | Probe 1 | Probe 2 | Probe 3 | Probe 4 | sens | spec vs norm-LGD | DFI vs norm-LGD |
| 20q gain | CEP 9 gain | 7p gain | 5q gain | 11 | 1 | 2 | 1 | 0.82 | 0.81 | 0.26 |
| 17p loss | 17q gain | CEP 9 gain | 5p gain | 14 | 4 | 4 | 1 | 0.76 | 0.85 | 0.28 |
| 17p loss | 20q gain | 17q gain | 5p gain | 13 | 14 | 4 | 1 | 0.77 | 0.84 | 0.28 |
| CEP 9 gain | 8q gain | 7p gain | 5q gain | 1 | 3 | 2 | 2 | 0.81 | 0.80 | 0.28 |
| CEP 9 gain | 7p gain | 5q gain | 5p gain | 1 | 2 | 1 | 2 | 0.79 | 0.81 | 0.28 |
| 17p loss | 17q gain | 5q gain | 5p gain | 15 | 4 | 2 | 1 | 0.76 | 0.85 | 0.28 |
| 17p loss | 20q gain | 17q gain | 9p gain | 15 | 12 | 4 | 1 | 0.78 | 0.83 | 0.28 |
| 17p loss | 17q gain | CEP 17 gain | 5p gain | 15 | 4 | 10 | 1 | 0.75 | 0.85 | 0.29 |
| 17p loss | 17q gain | 8q gain | 5p gain | 15 | 7 | 3 | 1 | 0.81 | 0.79 | 0.28 |
| 17p loss | 17q gain | 7p gain | 5p gain | 17 | 6 | 2 | 1 | 0.80 | 0.79 | 0.29 |
| 17p loss | 17q gain | CEP 7gain | 5p gain | 15 | 4 | 17 | 1 | 0.76 | 0.84 | 0.29 |
| 20q gain | 17q gain | 8q gain | 5p gain | 12 | 7 | 3 | 1 | 0.80 | 0.79 | 0.29 |
| 20q gain | 17q gain | 9p gain | 8q gain | 15 | 7 | 1 | 3 | 0.80 | 0.79 | 0.29 |
| 17p loss | 20q gain | 17q gain | 9p gain | 15 | 12 | 4 | 1 | 0.78 | 0.83 | 0.28 |
| 20q gain | 17q gain | 7p gain | 5p gain | 11 | 10 | 2 | 1 | 0.80 | 0.79 | 0.29 |
| 20q gain | 17q gain | CEP 7 gain | 5p gain | 14 | 4 | 14 | 1 | 0.84 | 0.75 | 0.30 |

TABLE 5C

| PROBE 1 | | PROBE 2 | | PROBE 3 | | PROBE 4 | | Cutoff (SO's + mean) | Normal | | normal + metaplasis | | normal + metaplasis + LGD | |
|---|---|---|---|---|---|---|---|---|---|---|---|---|---|---|
| | | | | | | | | | N | Specificity | N | Specificity | N | Specificity |
| 20q13 | gain | CEP 9 | gain | 7p12 | gain | 5q21-22 | gain | −0.2 | 30 | 0.900 | 58 | 0.6 | 61 | 0.776 |
| 17q/17p | gain | 17q11.2-12 | gain | CEP 9 | gain | 5p15 | gain | 0.0 | 31 | 0.935 | 57 | 0.9 | 60 | 0.837 |
| 17q/17p | gain | 20q13 | gain | 17q11.2-12 | gain | 5p15 | gain | 0.0 | 26 | 0.828 | 54 | 0.9 | 77 | 0.816 |
| CEP 9 | gain | 8q24.12-13 | gain | 7p12 | gain | 5q21-22 | gain | −0.2 | 30 | 0.933 | 58 | 0.8 | 81 | 0.753 |
| CEP 9 | gain | 7p12 | gain | 5q21-22 | gain | 5p15 | gain | −0.2 | 30 | 0.967 | 58 | 0.8 | 81 | 0.790 |
| 17q/17p | gain | 17q11.2-12 | gain | 5q21-22 | gain | 5p15 | gain | 0.0 | 31 | 0.935 | 57 | 0.9 | 80 | 0.837 |
| 17q/17p | gain | 20q13 | gain | 17q11.2-12 | gain | 9p21 | gain | 0.2 | 29 | 0.662 | 54 | 0.9 | 77 | 0.831 |
| 17p/CEP17 | loss | 17q11.2-12 | gain | CEP 17 | gain | 5p15 | gain | 0.0 | 31 | 0.966 | 57 | 0.9 | 80 | 0.825 |
| 17q/17p | gain | 17q11.2-12 | gain | 8q24.12-12 | gain | 5p15 | gain | 0.0 | 28 | 0.929 | 54 | 0.9 | 77 | 0.792 |
| 17q/17p | gain | 17q11.2-12 | gain | 7p12 | gain | 5p15 | gain | 0.0 | 28 | 0.929 | 54 | 0.9 | 77 | 0.806 |
| 17q/17p | gain | 17q11.2-12 | gain | CEP 7 | gain | 5p15 | gain | 0.0 | 28 | 0.929 | 54 | 0.9 | 77 | 0.805 |
| 20q13 | gain | 17q11.2-12 | gain | 8q24.12-13 | gain | 5p15 | gain | 0.0 | 28 | 0.964 | 54 | 0.9 | 77 | 0.805 |
| 20q13 | gain | 17q11.2-12 | gain | 9p21 | gain | 8q24.12-13 | gain | 0.0 | 29 | 0.828 | 54 | 0.9 | 77 | 0.782 |
| 17q/17p | gain | 20q13 | gain | 17q11.2-12 | gain | 9p21 | gain | 0.0 | 29 | 0.793 | 54 | 0.9 | 77 | 0.779 |
| 20q13 | gain | 17q11.2-12 | gain | 7p12 | gain | 5p16 | gain | 0.0 | 28 | 0.964 | 54 | 0.9 | 77 | 0.818 |
| 20q13 | gain | 17q11.2-12 | gain | CEP 7 | gain | 5p15 | gain | 0.0 | 28 | 0.964 | 54 | 0.9 | 77 | 0.818 |
| 20q13 | gain | 7p12 | gain | 5q21-22 | gain | 5p15 | gain | −0.2 | 30 | 0.900 | 58 | 0.9 | 81 | 0.753 |
| 17q/CEP17 | gain | 17p/CEP17 | loss | 17q11.2-12 | gain | 5p15 | gain | 0.2 | 31 | 0.935 | 58 | 0.9 | 79 | 0.835 |
| 17q/CEP17 | gain | 20q13 | gain | 17q11.2-12 | gain | 9p21 | gain | 0.2 | 29 | 0.793 | 54 | 0.8 | 77 | 0.706 |
| 17q/17p | gain | 17q11.2-12 | gain | 9p21 | gain | 5p15 | gain | 0.0 | 31 | 0.806 | 57 | 0.8 | 80 | 0.776 |
| CEP Y | gain | 21q13 | gain | 17q11.2-12 | gain | 5p15 | gain | 0.0 | 24 | 0.956 | 48 | 0.9 | 88 | 0.779 |
| 20q13 | gain | 17q11.2-12 | gain | CEP 17 | gain | 9p21 | gain | 0.0 | 29 | 0.826 | 54 | 0.9 | 77 | 0.818 |
| 20q13 | gain | 17q11.2-12 | gain | 9p21 | gain | CEP 9 | gain | 0.0 | 29 | 0.828 | 54 | 0.9 | 77 | 0.818 |
| 20q13 | gain | 17q11.2-12 | gain | 9p21 | gain | 5q21-22 | gain | 0.0 | 28 | 0.828 | 54 | 0.9 | 77 | 0.818 |
| 17p/CEP17 | gain | 20q13 | gain | CEP 17 | gain | 5p15 | gain | 0.0 | 28 | 1.000 | 54 | 0.9 | 77 | 0.831 |
| 20q13 | gain | 17q11.2-12 | gain | CEP 17 | gain | 5p15 | gain | 0.0 | 28 | 0.964 | 54 | 0.9 | 77 | 0.831 |
| 20q13 | gain | 17q11.2-12 | gain | 5q21-22 | gain | 5p16 | gain | 0.0 | 28 | 0.964 | 54 | 0.9 | 77 | 0.831 |
| 17Q/CEP17 | gain | 17p/CEP17 | loss | 9p21 | gain | 5q24.12-13 | gain | 0.0 | 29 | 0.793 | 54 | 0.9 | 77 | 0.753 |
| 17q11.2-12 | gain | CEP 9 | gain | 5q21-22 | gain | 5p15 | gain | 0.0 | 31 | 0.968 | 57 | 0.9 | 80 | 0.850 |
| 17q/CEP17 | gain | CEP Y | loss | 17q11.2-12 | gain | 5p15 | gain | 0.2 | 27 | 0.920 | 50 | 0.9 | 70 | 0.600 |

| PROBE 1 | | PROBE 2 | | PROBE 3 | | PROBE 4 | | Barrett's-No dysplasia | | | LGD | | | |
|---|---|---|---|---|---|---|---|---|---|---|---|---|---|---|
| | | | | | | | | N | Sensitivity | DFI vs norm | N | Sensitivity | DFI vs norm | DFI vs norm + mets |
| 20q13 | gain | CEP 9 | gain | 7p12 | gain | 5q21-22 | gain | 26 | 0.266 | 0.721 | 23 | 0.304 | 0.703 | 0.721 |
| 17q/17p | gain | 17q11.2-12 | gain | CEP 9 | gain | 5p15 | gain | 26 | 0.154 | 0.849 | 23 | 0.304 | 0.699 | 0.704 |
| 17q/17p | gain | 20q13 | gain | 17q11.2-12 | gain | 5p15 | gain | 26 | 0.192 | 0.811 | 23 | 0.304 | 0.699 | 0.708 |
| CEP 9 | gain | 8q24.12-13 | gain | 7p12 | gain | 5q21-22 | gain | 28 | 0.266 | 0.717 | 23 | 0.435 | 0.589 | 0.591 |
| CEP 9 | gain | 7p12 | gain | 5q21-22 | gain | 5p15 | gain | 28 | 0.266 | 0.715 | 23 | 0.348 | 0.653 | 0.670 |
| 17q/17p | gain | 17q11.2-12 | gain | 5q21-22 | gain | 5p15 | gain | 28 | 0.154 | 0.849 | 23 | 0.304 | 0.699 | 0.704 |
| 17q/17p | gain | 20q13 | gain | 17q11.2-12 | gain | 9p21 | gain | 25 | 0.080 | 0.930 | 23 | 0.304 | 0.709 | 0.704 |
| 17p/CEP17 | loss | 17q11.2-12 | gain | CEP 17 | gain | 5p15 | gain | 26 | 0.192 | 0.808 | 23 | 0.348 | 0.653 | 0.881 |
| 17q/17p | gain | 17q11.2-12 | gain | 8q24.12-12 | gain | 5p15 | gain | 26 | 0.269 | 0.734 | 23 | 0.304 | 0.699 | 0.715 |
| 17q/17p | gain | 17q11.2-12 | gain | 7p12 | gain | 5p15 | gain | 26 | 0.231 | 0.773 | 23 | 0.304 | 0.699 | 0.711 |
| 17q/17p | gain | 17q11.2-12 | gain | CEP 7 | gain | 5p15 | gain | 26 | 0.231 | 0.773 | 23 | 0.304 | 0.699 | 0.711 |
| 20q13 | gain | 17q11.2-12 | gain | 8q24.12-13 | gain | 5p15 | gain | 26 | 0.259 | 0.732 | 23 | 0.304 | 0.687 | 0.711 |
| 20q13 | gain | 17q11.2-12 | gain | 9p21 | gain | 8q24.12-13 | gain | 25 | 0.200 | 0.816 | 23 | 0.261 | 0.759 | 0.762 |
| 17q/17p | gain | 20q13 | gain | 17q11.2-12 | gain | 9p21 | gain | 25 | 0.180 | 0.665 | 23 | 0.304 | 0.726 | 0.720 |
| 20q13 | gain | 17q11.2-12 | gain | 7p12 | gain | 5p16 | gain | 26 | 0.231 | 0.770 | 23 | 0.304 | 0.697 | 0.706 |
| 20q13 | gain | 17q11.2-12 | gain | CEP 7 | gain | 5p15 | gain | 26 | 0.231 | 0.770 | 23 | 0.304 | 0.697 | 0.706 |
| 20q13 | gain | 7p12 | gain | 5q21-22 | gain | 5p15 | gain | 26 | 0.321 | 0.656 | 23 | 0.346 | 0.600 | 0.884 |
| 17q/CEP17 | gain | 17p/CEP17 | loss | 17q11.2-12 | gain | 5p15 | gain | 25 | 0.120 | 0.882 | 23 | 0.346 | 0.655 | 0.658 |
| 17q/CEP17 | gain | 20q13 | gain | 17q11.2-12 | gain | 9p21 | gain | 25 | 0.100 | 0.665 | 23 | 0.348 | 0.884 | 0.878 |
| 17q/17p | gain | 17q11.2-12 | gain | 9p21 | gain | 5p15 | gain | 26 | 0.192 | 0.831 | 23 | 0.304 | 0.722 | 0.722 |
| CEP Y | gain | 21q13 | gain | 17q11.2-12 | gain | 5p15 | gain | 24 | 0.206 | 0.793 | 20 | 0.450 | 0.552 | 0.584 |
| 20q13 | gain | 17q11.2-12 | gain | CEP 17 | gain | 9p21 | gain | 25 | 0.120 | 0.697 | 23 | 0.261 | 0.769 | 0.754 |
| 20q13 | gain | 17q11.2-12 | gain | 9p21 | gain | CEP 9 | gain | 25 | 0.120 | 0.697 | 23 | 0.261 | 0.759 | 0.754 |
| 20q13 | gain | 17q11.2-12 | gain | 9p21 | gain | 5q21-22 | gain | 25 | 0.120 | 0.697 | 23 | 0.261 | 0.759 | 0.754 |
| 17p/CEP17 | gain | 20q13 | gain | CEP 17 | gain | 5p15 | gain | 26 | 0.192 | 0.606 | 23 | 0.348 | 0.652 | 0.659 |
| 20q13 | gain | 17q11.2-12 | gain | CEP 17 | gain | 5p15 | gain | 26 | 0.192 | 0.808 | 23 | 0.304 | 0.697 | 0.704 |
| 20q13 | gain | 17q11.2-12 | gain | 5q21-22 | gain | 5p16 | gain | 26 | 0.192 | 0.808 | 23 | 0.304 | 0.697 | 0.704 |
| 17Q/CEP17 | gain | 17p/CEP17 | loss | 9p21 | gain | 5q24.12-13 | gain | 25 | 0.200 | 0.825 | 23 | 0.348 | 0.684 | 0.683 |
| 17q11.2-12 | gain | CEP 9 | gain | 5q21-22 | gain | 5p15 | gain | 26 | 0.154 | 0.647 | 23 | 0.304 | 0.696 | 0.701 |
| 17q/CEP17 | gain | CEP Y | loss | 17q11.2-12 | gain | 5p15 | gain | 23 | 0.130 | 0.873 | 20 | 0.460 | 0.555 | 0.559 |

TABLE 5C-continued

| PROBE 1 | | PROBE 2 | | PROBE 3 | | PROBE 4 | | HGD N | Sensitivity | DFI vs norm | DFI vs norm + mets + LGD | Adenocarcinoma N | Sensitivity | DFI vs norm |
|---|---|---|---|---|---|---|---|---|---|---|---|---|---|---|
| 20q13 | gain | CEP 9 | gain | 7p12 | gain | 5q21-22 | gain | 67 | 0.806 | 0.218 | 0.295 | 16 | 0.938 | 0.118 |
| 17q/17p | gain | 17q11.2-12 | gain | CEP 9 | gain | 5p15 | gain | 67 | 0.716 | 0.291 | 0.327 | 16 | 0.938 | 0.090 |
| 17q/17p | gain | 20q13 | gain | 17q11.2-12 | gain | 5p15 | gain | 67 | 0.731 | 0.276 | 0.324 | 16 | 0.936 | 0.095 |
| CEP 9 | gain | 8q24.12-13 | gain | 7p12 | gain | 5q21-22 | gain | 67 | 0.806 | 0.205 | 0.314 | 16 | 0.936 | 0.091 |
| CEP 9 | gain | 7p12 | gain | 5q21-22 | gain | 5p15 | gain | 67 | 0.701 | 0.241 | 0.318 | 17 | 0.852 | 0.122 |
| 17q/17p | gain | 17q11.2-12 | gain | 5q21-22 | gain | 5p15 | gain | 67 | 0.701 | 0.305 | 0.340 | 16 | 0.938 | 0.090 |
| 17q/17p | gain | 20q13 | gain | 17q11.2-12 | gain | 9p21 | gain | 67 | 0.701 | 0.329 | 0.343 | 15 | 0.933 | 0.153 |
| 17p/CEP17 | loss | 17q11.2-12 | gain | CEP 17 | gain | 5p15 | gain | 67 | 0.701 | 0.300 | 0.346 | 16 | 0.938 | 0.070 |
| 17q/17p | gain | 17q11.2-12 | gain | 8q24.12-12 | gain | 5p15 | gain | 67 | 0.731 | 0.276 | 0.340 | 16 | 0.938 | 0.095 |
| 17q/17p | gain | 17q11.2-12 | gain | 7p12 | gain | 5p15 | gain | 67 | 0.716 | 0.292 | 0.344 | 15 | 0.938 | 0.095 |
| 17q/17p | gain | 17q11.2-12 | gain | CEP 7 | gain | 5p15 | gain | 67 | 0.716 | 0.292 | 0.344 | 18 | 0.933 | 0.095 |
| 20q13 | gain | 17q11.2-12 | gain | 8q24.12-13 | gain | 5p15 | gain | 67 | 0.716 | 0.266 | 0.344 | 18 | 0.938 | 0.072 |
| 20q13 | gain | 17q11.2-12 | gain | 9p21 | gain | 8q24.12-13 | gain | 67 | 0.731 | 0.319 | 0.340 | 15 | 0.936 | 0.185 |
| 17q/17p | gain | 20q13 | gain | 17q11.2-12 | gain | 9p21 | gain | 67 | 0.746 | 0.327 | 0.336 | 15 | 0.934 | 0.217 |
| 20q13 | gain | 17q11.2-12 | gain | 7p12 | gain | 5p16 | gain | 67 | 0.701 | 0.301 | 0.350 | 16 | 0.938 | 0.072 |
| 20q13 | gain | 17q11.2-12 | gain | CEP 7 | gain | 5p15 | gain | 67 | 0.701 | 0.301 | 0.350 | 16 | 0.934 | 0.072 |
| 20q13 | gain | 7p12 | gain | 5q21-22 | gain | 5p15 | gain | 67 | 0.776 | 0.245 | 0.333 | 17 | 0.941 | 0.116 |
| 17q/CEP17 | gain | 17p/CEP17 | loss | 17q11.2-12 | gain | 5p15 | gain | 67 | 0.887 | 0.320 | 0.354 | 16 | 0.938 | 0.090 |
| 17q/CEP17 | gain | 20q13 | gain | 17q11.2-12 | gain | 9p21 | gain | 67 | 0.761 | 0.318 | 0.334 | 15 | 0.933 | 0.217 |
| 17q/17p | gain | 17q11.2-12 | gain | 9p21 | gain | 5p15 | gain | 67 | 0.748 | 0.319 | 0.339 | 16 | 0.936 | 0.203 |
| CEP Y | gain | 21q13 | gain | 17q11.2-12 | gain | 5p15 | gain | 65 | 0.738 | 0.265 | 0.342 | 16 | 0.938 | 0.075 |
| 20q13 | gain | 17q11.2-12 | gain | CEP 17 | gain | 9p21 | gain | 67 | 0.701 | 0.345 | 0.350 | 15 | 0.933 | 0.185 |
| 20q13 | gain | 17q11.2-12 | gain | 9p21 | gain | CEP 9 | gain | 67 | 0.701 | 0.345 | 0.350 | 15 | 0.933 | 0.185 |
| 20q13 | gain | 17q11.2-12 | gain | 9p21 | gain | 5q21-22 | gain | 67 | 0.701 | 0.345 | 0.350 | 15 | 0.933 | 0.185 |
| 17p/CEP17 | gain | 20q13 | gain | CEP 17 | gain | 5p15 | gain | 67 | 0.701 | 0.299 | 0.343 | 16 | 0.875 | 0.125 |
| 20q13 | gain | 17q11.2-12 | gain | CEP 17 | gain | 5p15 | gain | 67 | 0.687 | 0.315 | 0.356 | 16 | 0.938 | 0.072 |
| 20q13 | gain | 17q11.2-12 | gain | 5q21-22 | gain | 5p16 | gain | 67 | 0.687 | 0.315 | 0.356 | 16 | 0.938 | 0.072 |
| 17Q/CEP17 | gain | 17p/CEP17 | loss | 9p21 | gain | 5q24.12-13 | gain | 67 | 0.776 | 0.305 | 0.333 | 15 | 0.933 | 0.217 |
| 17q11.2-12 | gain | CEP 9 | gain | 5q21-22 | gain | 5p15 | gain | 67 | 0.872 | 0.330 | 0.361 | 16 | 0.933 | 0.070 |
| 17q/CEP17 | gain | CEP Y | loss | 17q11.2-12 | gain | 5p15 | gain | 66 | 0.712 | 0.297 | 0.351 | 16 | 0.938 | 0.097 |

| PROBE 1 | | PROBE 2 | | PROBE 3 | | PROBE 4 | | Adenocarcinoma DFI vs norm + mets + LGD + HGD | Adenocarcinoma + all HGD N | Sensitivity | DFI vs norm | DFI vs norm + mets + LGD |
|---|---|---|---|---|---|---|---|---|---|---|---|---|
| 20q13 | gain | CEP 9 | gain | 7p12 | gain | 5q21-22 | gain | 0.490 | 83 | 0.831 | 0.196 | 0.279 |
| 17q/17p | gain | 17q11.2-12 | gain | CEP 9 | gain | 5p15 | gain | 0.420 | 83 | 0.759 | 0.249 | 0.291 |
| 17q/17p | gain | 20q13 | gain | 17q11.2-12 | gain | 5p15 | gain | 0.442 | 83 | 0.771 | 0.240 | 0.292 |
| CEP 9 | gain | 8q24.12-13 | gain | 7p12 | gain | 5q21-22 | gain | 0.504 | 83 | 0.631 | 0.181 | 0.299 |
| CEP 9 | gain | 7p12 | gain | 5q21-22 | gain | 5p15 | gain | 0.474 | 84 | 0.786 | 0.217 | 0.300 |
| 17q/17p | gain | 17q11.2-12 | gain | 5q21-22 | gain | 5p15 | gain | 0.413 | 83 | 0.747 | 0.261 | 0.301 |
| 17q/17p | gain | 20q13 | gain | 17q11.2-12 | gain | 9p21 | gain | 0.422 | 82 | 0.744 | 0.291 | 0.307 |
| 17p/CEP17 | loss | 17q11.2-12 | gain | CEP 17 | gain | 5p15 | gain | 0.420 | 83 | 0.747 | 0.255 | 0.308 |
| 17q/17p | gain | 17q11.2-12 | gain | 8q24.12-12 | gain | 5p15 | gain | 0.456 | 83 | 0.771 | 0.240 | 0.309 |
| 17q/17p | gain | 17q11.2-12 | gain | 7p12 | gain | 5p15 | gain | 0.442 | 83 | 0.759 | 0.251 | 0.310 |
| 17q/17p | gain | 17q11.2-12 | gain | CEP 7 | gain | 5p15 | gain | 0.442 | 83 | 0.759 | 0.251 | 0.310 |
| 20q13 | gain | 17q11.2-12 | gain | 8q24.12-13 | gain | 5p15 | gain | 0.442 | 83 | 0.759 | 0.244 | 0.310 |
| 20q13 | gain | 17q11.2-12 | gain | 9p21 | gain | 8q24.12-13 | gain | 0.456 | 82 | 0.766 | 0.269 | 0.311 |
| 17q/17p | gain | 20q13 | gain | 17q11.2-12 | gain | 9p21 | gain | 0.470 | 82 | 0.780 | 0.302 | 0.311 |
| 20q13 | gain | 17q11.2-12 | gain | 7p12 | gain | 5p16 | gain | 0.426 | 83 | 0.747 | 0.256 | 0.312 |
| 20q13 | gain | 17q11.2-12 | gain | CEP 7 | gain | 5p15 | gain | 0.420 | 83 | 0.747 | 0.256 | 0.312 |
| 20q13 | gain | 7p12 | gain | 5q21-22 | gain | 5p15 | gain | 0.490 | 64 | 0.510 | 0.215 | 0.312 |
| 17q/CEP17 | gain | 17p/CEP17 | loss | 17q11.2-12 | gain | 5p15 | gain | 0.409 | 63 | 0.735 | 0.273 | 0.312 |
| 17q/CEP17 | gain | 20q13 | gain | 17q11.2-12 | gain | 9p21 | gain | 0.484 | 62 | 0.793 | 0.283 | 0.312 |
| 17q/17p | gain | 17q11.2-12 | gain | 9p21 | gain | 5p15 | gain | 0.487 | 63 | 0.783 | 0.291 | 0.313 |
| CEP Y | gain | 21q13 | gain | 17q11.2-12 | gain | 5p15 | gain | 0.476 | 81 | 0.778 | 0.226 | 0.313 |
| 20q13 | gain | 17q11.2-12 | gain | CEP 17 | gain | 9p21 | gain | 0.429 | 82 | 0.744 | 0.309 | 0.314 |
| 20q13 | gain | 17q11.2-12 | gain | 9p21 | gain | CEP 9 | gain | 0.429 | 82 | 0.744 | 0.309 | 0.314 |
| 20q13 | gain | 17q11.2-12 | gain | 9p21 | gain | 5q21-22 | gain | 0.429 | 82 | 0.744 | 0.309 | 0.314 |
| 17p/CEP17 | gain | 20q13 | gain | CEP 17 | gain | 5p15 | gain | 0.435 | 83 | 0.735 | 0.265 | 0.314 |
| 20q13 | gain | 17q11.2-12 | gain | CEP 17 | gain | 5p15 | gain | 0.414 | 83 | 0.735 | 0.267 | 0.314 |
| 20q13 | gain | 17q11.2-12 | gain | 5q21-22 | gain | 5p16 | gain | 0.414 | 83 | 0.735 | 0.267 | 0.314 |
| 17Q/CEP17 | gain | 17p/CEP17 | loss | 9p21 | gain | 5q24.12-13 | gain | 0.496 | 82 | 0.805 | 0.284 | 0.315 |
| 17q11.2-12 | gain | CEP 9 | gain | 5q21-22 | gain | 5p15 | gain | 0.383 | 83 | 0.723 | 0.279 | 0.315 |
| 17q/CEP17 | gain | CEP Y | loss | 17q11.2-12 | gain | 5p15 | gain | 0.453 | 82 | 0.758 | 0.255 | 0.315 |

TABLE 6A

Cutoffs based on means (x) and multiples (n) of standard deviations (s) of the IM specimen group and resulting performance characteristics of 4-probe combinations for discriminating LGD specimens from the combined group of normal and IM specimens.

| | | | | | | | | | | LGD | | | | | | | |
|---|---|---|---|---|---|---|---|---|---|---|---|---|---|---|---|---|---|
| Probe 1 | Probe 2 | Probe 3 | Probe 4 | C/O n | IM N | sens | N | sens | spec vs norm | DFI vs norm | spec vs norm-IM | DFI vs norm-IM | HGD N | sens | EA N | sens | EA + HGD N | sens |
| 9p loss | CEP Y loss | CEP 9 gain | CEP 7 loss | 1.2 | 25 | 0.24 | 20 | 0.70 | 0.96 | 0.30 | 0.86 | 0.33 | 65 | 0.66 | 15 | 0.80 | 80 | 0.69 |
| CEP Y loss | 9p loss | CEP 7 loss | 5q gain | 1.2 | 25 | 0.24 | 20 | 0.70 | 0.96 | 0.30 | 0.86 | 0.33 | 64 | 0.67 | 15 | 0.80 | 79 | 0.70 |
| CEP Y loss | 17q loss | 9p loss | CEP 7 loss | 1.2 | 25 | 0.28 | 18 | 0.72 | 0.88 | 0.30 | 0.80 | 0.34 | 63 | 0.57 | 14 | 0.57 | 77 | 0.57 |
| CEP Y loss | 20q gain | 9p loss | CEP 7 loss | 1.4 | 25 | 0.32 | 20 | 0.70 | 0.96 | 0.30 | 0.82 | 0.35 | 65 | 0.66 | 15 | 0.67 | 80 | 0.66 |
| CEP Y loss | 9p loss | 7p loss | CEP 7 loss | 1.2 | 25 | 0.28 | 19 | 0.68 | 0.96 | 0.32 | 0.84 | 0.36 | 63 | 0.56 | 14 | 0.57 | 77 | 0.56 |
| CEP Y loss | 9p loss | 8q gain | CEP 7 loss | 1.2 | 25 | 0.24 | 18 | 0.67 | 0.96 | 0.34 | 0.86 | 0.36 | 64 | 0.56 | 15 | 0.60 | 79 | 0.57 |
| 20q gain | 17q gain | 9p loss | 8g gain | 0.2 | 26 | 0.35 | 23 | 0.61 | 0.76 | 0.46 | 0.71 | 0.49 | 67 | 0.85 | 17 | 0.94 | 84 | 0.87 |

TABLE 6B

Refined cutoffs and performance characteristics of 4-probe combinations for discriminating LGD specimens from the combined group of normal and IM specimens.

| Probes | | | | Percent Cell Cutoffs | | | | Performance | | |
|---|---|---|---|---|---|---|---|---|---|---|
| 1 | 2 | 3 | 4 | Probe 1 | Probe 2 | Probe 3 | Probe 4 | sens | spec vs norm-IM | DFI vs norm-IM |
| 9p loss | CEP Y loss | CEP 9 gain | CEP 7 loss | 14 | 13 | 1 | 4 | 0.80 | 0.80 | 0.29 |
| CEP Y loss | 9p loss | CEP 7 loss | 5q gain | 13 | 13 | 4 | 2 | 0.75 | 0.82 | 0.31 |
| CEP Y loss | 17q loss | 9p loss | CEP 7 loss | 4 | 6 | 12 | 4 | 0.75 | 0.76 | 0.35 |
| CEP Y loss | 20q gain | 9p loss | CEP 7 loss | | | | | | | |
| CEP Y loss | 9p loss | 7p loss | CEP 7 loss | | | | | | | |
| CEP Y loss | 9p loss | 8q gain | CEP 7 loss | | | | | | | |
| 20q gain | 17q gain | 9p loss | 8q gain | 1 | 6 | 12 | 7 | 0.70 | 0.73 | 0.41 |

TABLE 6C

| PROBE 1 | | PROBE 2 | | PROBE 3 | | PROBE 4 | | Cutoff (SD's + mean) | Normal N | Specificity | normal + metaplasia N | Specificity | normal + metaplasia + LGD N | Specificity |
|---|---|---|---|---|---|---|---|---|---|---|---|---|---|---|
| 9p/CEP9 | loss | CEP Y | loss | CEP 9 | gain | CEP 7 | loss | 1.20 | 24 | 0.958 | 49 | 0.857 | 69 | 0.696 |
| CEP Y | loss | 9p21 | loss | CEP 9 | gain | CEP 7 | loss | 1.20 | 24 | 0.956 | 49 | 0.857 | 69 | 0.696 |
| CEP Y | loss | 9p21 | loss | CEP 7 | loss | 5q21-22 | gain | 1.20 | 24 | 0.958 | 49 | 0.857 | 69 | 0.696 |
| CEP Y | loss | 9p21 | loss | CEP 7 | loss | 5p15 | gain | 1.20 | 24 | 0.958 | 49 | 0.857 | 69 | 0.696 |
| CEP Y | loss | 17q11.2-12 | loss | 9p21 | loss | CEP 7 | loss | 1.20 | 24 | 0.875 | 49 | 0.798 | 67 | 0.657 |
| CEP Y | loss | 20q13 | gain | 9p21 | loss | CEP 7 | loss | 1.40 | 24 | 0.958 | 49 | 0.816 | 68 | 0.657 |
| CEP Y | loss | 9p21 | loss | 7p12 | loss | CEP 7 | loss | 1.20 | 24 | 0.958 | 49 | 0.837 | 68 | 0.691 |
| CEP Y | loss | 9p21 | loss | CEP 7 | gain | CEP 7 | loss | 1.40 | 24 | 0.958 | 49 | 0.837 | 68 | 0.691 |
| CEP Y | loss | CEP 17 | loss | 9p21 | loss | CEP 7 | loss | 1.20 | 24 | 0.875 | 49 | 0.755 | 68 | 0.618 |
| 9p/CEP9 | loss | CEP Y | loss | 9p21 | loss | CEP 7 | loss | 1.20 | 24 | 0.958 | 49 | 0.857 | 67 | 0.718 |
| 7p/CEP7 | gain | CEP Y | loss | 9p21 | loss | CEP 7 | loss | 1.20 | 24 | 0.958 | 49 | 0.857 | 67 | 0.718 |
| CEP Y | loss | 17p13.1 | loss | 9p21 | loss | CEP 7 | loss | 1.20 | 24 | 0.958 | 49 | 0.857 | 67 | 0.718 |
| CEP Y | loss | 9p21 | loss | 8q24.12-13 | gain | CEP 7 | loss | 1.20 | 24 | 0.958 | 49 | 0.857 | 67 | 0.718 |

| PROBE 1 | | PROBE 2 | | PROBE 3 | | PROBE 4 | | Barnatt's-No dysplasia N | Sensitivity | DFI vs norm | LGD N | Sensitivity | DFI vs norm | DFI vs norm + mets |
|---|---|---|---|---|---|---|---|---|---|---|---|---|---|---|
| 9p/CEP9 | loss | CEP Y | loss | CEP 9 | gain | CEP 7 | loss | 25 | 0.240 | 0.761 | 20 | 0.700 | 0.303 | 0.332 |
| CEP Y | loss | 9p21 | loss | CEP 9 | gain | CEP 7 | loss | 25 | 0.240 | 0.761 | 20 | 0.700 | 0.303 | 0.332 |
| CEP Y | loss | 9p21 | loss | CEP 7 | loss | 5q21-22 | gain | 25 | 0.240 | 0.761 | 20 | 0.700 | 0.303 | 0.332 |
| CEP Y | loss | 9p21 | loss | CEP 7 | loss | 5p15 | gain | 25 | 0.240 | 0.761 | 20 | 0.700 | 0.303 | 0.332 |

TABLE 6C-continued

| PROBE 1 | | PROBE 2 | | PROBE 3 | | PROBE 4 | | N | | | | | |
|---|---|---|---|---|---|---|---|---|---|---|---|---|---|
| CEP Y | loss | 17q11.2-12 | loss | 9p21 | loss | CEP 7 | loss | 25 | 0.280 | 0.731 | 18 | 0.722 | 0.306 | 0.345 |
| CEP Y | loss | 20q13 | gain | 9p21 | loss | CEP 7 | loss | 25 | 0.320 | 0.681 | 20 | 0.700 | 0.303 | 0.352 |
| CEP Y | loss | 9p21 | loss | 7p12 | loss | CEP 7 | loss | 25 | 0.280 | 0.721 | 19 | 0.884 | 0.319 | 0.355 |
| CEP Y | loss | 9p21 | loss | CEP 7 | loss | CEP 7 | gain | 25 | 0.280 | 0.721 | 19 | 0.884 | 0.319 | 0.355 |
| CEP Y | loss | CEP 17 | loss | 9p21 | loss | CEP 7 | loss | 25 | 0.380 | 0.652 | 19 | 0.737 | 0.291 | 0.358 |
| 9p/CEP9 | loss | CEP Y | loss | 9p21 | loss | CEP 7 | loss | 25 | 0.240 | 0.761 | 18 | 0.667 | 0.338 | 0.363 |
| 7p/CEP7 | gain | CEP Y | loss | 9p21 | loss | CEP 7 | loss | 25 | 0.240 | 0.761 | 18 | 0.667 | 0.338 | 0.363 |
| CEP Y | loss | 17p13.1 | loss | 9p21 | loss | CEP 7 | loss | 25 | 0.240 | 0.761 | 18 | 0.667 | 0.238 | 0.363 |
| CEP Y | loss | 9p21 | loss | 8q24.12-13 | gain | CEP 7 | loss | 25 | 0.240 | 0.761 | 18 | 0.667 | 0.336 | 0.363 |

| | | | | | | | | HGD | | | Adenocarcinoma | | |
|---|---|---|---|---|---|---|---|---|---|---|---|---|---|
| PROBE 1 | | PROBE 2 | | PROBE 3 | | PROBE 4 | | N | Sensitivity | DFI vs norm | DFI vs norm + mets + LGD | N | Sensitivity | DFI vs norm |
| 9p/CEP9 | loss | CEP Y | loss | CEP 9 | gain | CEP 7 | loss | 65 | 0.662 | 0.341 | 0.455 | 15 | 0.800 | 0.204 |
| CEP Y | loss | 9p21 | loss | CEP 9 | gain | CEP 7 | loss | 65 | 0.662 | 0.341 | 0.455 | 15 | 0.800 | 0.204 |
| CEP Y | loss | 9p21 | loss | CEP 7 | loss | 5q21-22 | gain | 64 | 0.672 | 0.331 | 0.448 | 15 | 0.800 | 0.204 |
| CEP Y | loss | 9p21 | loss | CEP 7 | loss | 5p15 | gain | 64 | 0.672 | 0.331 | 0.448 | 15 | 0.613 | 0.192 |
| CEP Y | loss | 17q11.2-12 | loss | 9p21 | loss | CEP 7 | loss | 63 | 0.571 | 0.446 | 0.549 | 14 | 0.571 | 0.446 |
| CEP Y | loss | 20q13 | gain | 9p21 | loss | CEP 7 | loss | 65 | 0.682 | 0.341 | 0.475 | 15 | 0.687 | 0.336 |
| CEP Y | loss | 9p21 | loss | 7p12 | loss | CEP 7 | loss | 63 | 0.558 | 0.446 | 0.541 | 14 | 0.571 | 0.431 |
| CEP Y | loss | 9p21 | loss | CEP 7 | loss | CEP 7 | gain | 66 | 0.621 | 0.381 | 0.489 | 15 | 0.687 | 0.338 |
| CEP Y | loss | CEP 17 | loss | 9p21 | loss | CEP 7 | loss | 64 | 0.683 | 0.455 | 0.581 | 14 | 0.571 | 0.448 |
| 9p/CEP9 | loss | CEP Y | loss | 9p21 | loss | CEP 7 | loss | 63 | 0.506 | 0.494 | 0.588 | 14 | 0.571 | 0.431 |
| 7p/CEP7 | gain | CEP Y | loss | 9p21 | loss | CEP 7 | loss | 63 | 0.506 | 0.494 | 0.588 | 15 | 0.733 | 0.270 |
| CEP Y | loss | 17p13.1 | loss | 9p21 | loss | CEP 7 | loss | 63 | 0.540 | 0.482 | 0.541 | 14 | 0.571 | 0.431 |
| CEP Y | loss | 9p21 | loss | 8q24.12-13 | gain | CEP 7 | loss | 64 | 0.583 | 0.439 | 0.521 | 15 | 0.800 | 0.402 |

| | | | | | | | | Adenocarcinoma | Adenocarcinoma + all HGD | | | |
|---|---|---|---|---|---|---|---|---|---|---|---|---|
| PROBE 1 | | PROBE 2 | | PROBE 3 | | PROBE 4 | | DFI vs norm + mets + LGD + HGD | N | Sensitivity | DFI vs norm | DFI vs norm + mets + LGD |
| 9p/CEP9 | loss | CEP Y | loss | CEP 9 | gain | CEP 7 | loss | 0.518 | 80 | 0.688 | 0.315 | 0.436 |
| CEP Y | loss | 9p21 | loss | CEP 9 | gain | CEP 7 | loss | 0.518 | 80 | 0.688 | 0.315 | 0.436 |
| CEP Y | loss | 9p21 | loss | CEP 7 | loss | 5q21-22 | gain | 0.521 | 79 | 0.696 | 0.307 | 0.430 |
| CEP Y | loss | 9p21 | loss | CEP 7 | loss | 5p15 | gain | 0.518 | 80 | 0.700 | 0.303 | 0.427 |
| CEP Y | loss | 17q11.2-12 | loss | 9p21 | loss | CEP 7 | loss | 0.624 | 77 | 0.671 | 0.448 | 0.549 |
| CEP Y | loss | 20q13 | gain | 9p21 | loss | CEP 7 | loss | 0.595 | 80 | 0.663 | 0.340 | 0.474 |
| CEP Y | loss | 9p21 | loss | 7p12 | loss | CEP 7 | loss | 0.605 | 77 | 0.558 | 0.444 | 0.539 |
| CEP Y | loss | 9p21 | loss | CEP 7 | loss | CEP 7 | gain | 0.570 | 81 | 0.630 | 0.373 | 0.462 |
| CEP Y | loss | CEP 17 | loss | 9p21 | loss | CEP 7 | loss | 0.636 | 78 | 0.564 | 0.453 | 0.580 |
| 9p/CEP9 | loss | CEP Y | loss | 9p21 | loss | CEP 7 | loss | 0.581 | 77 | 0.619 | 0.482 | 0.558 |
| 7p/CEP7 | gain | CEP Y | loss | 9p21 | loss | CEP 7 | loss | 0.474 | 78 | 0.551 | 0.451 | 0.531 |
| CEP Y | loss | 17p13.1 | loss | 9p21 | loss | CEP 7 | loss | 0.692 | 77 | 0.645 | 0.456 | 0.538 |
| CEP Y | loss | 9p21 | loss | 8q24.12-13 | gain | CEP 7 | loss | 0.580 | 79 | 0.570 | 0.432 | 0.515 |

Probe Set 8q24.12-13, 9p21, 17q11.2-12 and 20q13

Figure 4:
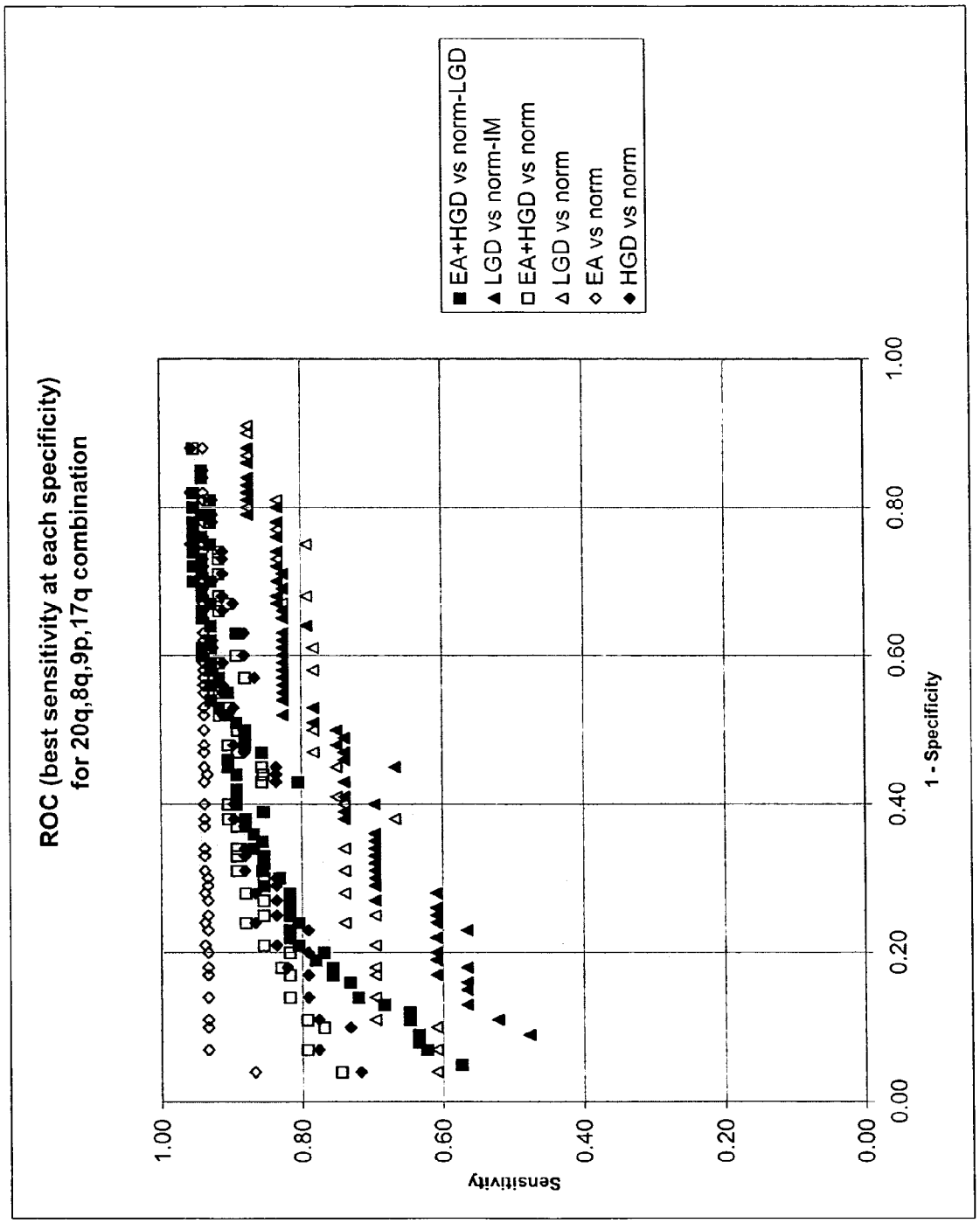
FIG. 4 shows ROC curves that illustrate the relationships between sensitivity and specificity for individually detecting EA, HGD, LGD, and EA+HGD specimens relative to normal specimens, as well as detecting EA+HGD specimens relative to normal+IM+LGD specimens, as well as LGD relative to normal+IM specimens for a probe set of 8q24.12-13, 9p21, 17q11.2-12 and 20q13.

One of the best performing probe sets in both FIGS. 2 and 3 is the set of 8q24.12-13, 9p21, 17q11.2-12 and 20q13. ROC curves for just this probe combination are shown in FIG. 4. These ROC curves include the specificities and sensitivities for detecting EA, HGD, and LGD individually versus normal specimens, as well as EA+HGD versus normal specimens. Equal sensitivity and specificity occurs at about 80% (DFI=0.29) for EA+HGD versus normal+IM+LGD specimens, and at about 70% (DFI=0.42) for LGD versus normal+ IM specimens. Cutoffs used to achieve these DFI values are listed in Tables 5 and 6 (refined cutoff values). ROC curves for detecting EA versus normal specimens showed better performance than similar curves for HGD vs. normal specimens, and ROC curves for HGD versus normal specimens showed better performance than curves for LGD vs. normal. This is expected since EA specimens on average have higher percentages of abnormal cells than HGD specimens, and HGD specimens have higher percentages of abnormal cells than LGD specimens (see FIGS. 1A and 1B), thereby permitting the use of higher cutoffs to improve specificity while minimally decreasing sensitivity. Performance is lower for EA+HGD versus normal+IM+LGD specimens than for EA+HGD versus only normal specimens. This is not surprising since it is likely that some of the patients in the LGD group in particular had HGD lesions that were not biopsied but were sampled by FISH. These cases would appear as false positive results by FISH and consequently appeared as false positives in our analyses (see below).

Anticipatory Positive Cases

"False positive" FISH results (i.e., positive FISH result for a patient with a negative pathology result) were expected and observed through the course of the study. Possible explanations for "false positive" FISH results include: 1) the FISH result is truly falsely positive for abnormality, 2) FISH is detecting a lesion that was not biopsied due to incomplete sampling by endoscopist), 3) the biopsy was incorrectly interpreted as normal by the pathologist, or 4) FISH is detecting genetic changes before histological changes can be identified. A significant proportion of the "false positive" FISH results are not believed to be true false positive results but rather believed to represent cases in which FISH has detected an abnormality that was not detected by the "gold standard" (i.e., biopsy). This phenomenon has previously been observed when using FISH to detect recurrent bladder cancer in patients being monitored for tumor recurrence. Long-term follow-up of these patients has shown that a high proportion of these patients with apparent false positive FISH results eventually develop biopsy proven tumor. For this reason, "false positive" results are sometimes referred to as anticipatory positive FISH results since they frequently represent cases in which tumor has been detected before it can be identified by other means. Follow-up data is needed to determine if the "false positive" FISH results observed with the Barrett's esophagus probe sets are indeed anticipatory positives.

Example 2

Esophageal Cancer Detection

As a non-limiting exemplification of the present invention, the four-color probe set 8q24.12-13, 9p21, 17q11.2-12 and 20q13, described in Example 1 above, was used to assess esophageal brushing samples for the presence of cells that have chromosomal abnormalities consistent with a diagnosis of LGD, HGD, or EA. Samples were prepared for FISH hybridization and subject to hybridization with the probe set as described in the probe selection study (Example 1, above) and as described below. For cases in which the initial 100-cell enumeration was negative for polysomy, the remainder of the slide was scanned for morphologically abnormal cells (e.g., nuclear enlargement, nuclear irregularity and mottled chromatin staining) and their FISH hybridization patterns of these cells also recorded.

Cell Harvest

A 50 mL centrifuge and a 1.8 ml micro-centrifuge tube were labeled with appropriate patient identifiers. The specimen container (PreservCyt™ solution container containing the esophageal brush) was vigorously shaken by hand to resuspend the cells. The solution in the specimen container was transferred to the 50 mL centrifuge tube, making sure to leave the cytologic brush in the specimen container. Twenty mL of 3:1 methanol:acetic acid fixative was added to the specimen container. The contents of the specimen container (fixative and the brush) were then transferred to a Petri dish. The brush was manually scraped with a scalpel into the fixative and the solution in the Petri dish was then put back into the specimen container. The brush was discarded. The solution in the specimen container was then transferred to the labeled 50 mL tube. Ten ml of 3:1 methanol:acetic acid fixative was added to the specimen container. The specimen container was vigorously shaken by hand to remove any residual cells and transferred to the 50 ml tube. The specimen container was discarded.

The solution in the 50 mL tube was centrifuged at 800 g for eight minutes. All but about 5 ml of the supernatant was then removed by vacuum aspiration. Ten ml of 3:1 methanol:acetic acid was added to the 50 mL tube and the cell pellet was gently resuspended. The solution was then centrifuged at 300 g for eight minutes. The supernatant was then aspirated, making sure to leave about 2 mL of the solution on top of the pellet. The pellet was again resuspended. The specimen was transferred to a pre-labeled 1.8 ml micro-centrifuge tube using a disposable pipette and stored at 4° C. For long term preservation, the specimen was stored in the same 1.8 ml micro-centrifuge tube at −70° C., making sure that the tube was filled to the top with 3:1 methanol:acetic acid fixative before storage.

Slide Preparation

The 1.8 ml micro-centrifuge tube containing the desired specimen was placed into a balanced centrifuge and spun at 800 g for two minutes. A disposable pipette was used to remove most of the top layer of fixative, usually to the 0.25 ml line. A slide labeled with appropriate patient identifiers was placed on a 45° C. hot plate. A pipette was used to resuspend the cell pellet and 10 μl of the solution was pipetted onto a 10 mm etched ring of the slide. The slide was then examined under a phase contrast microscope to assess cellularity (i.e., the density of the cells). If the cellularity was inadequate additional amounts of the pellet were dropped onto the slide 10 μl at a time until adequate cellularity (the greatest number of cells per ring with minimal cell overlap) was achieved. If the cellularity was too high the specimen pellet was diluted with 3:1 methanol:acetic acid fixative and the above process repeated on a new etched ring.

Pretreatment

If a slide was prepared on the same day of hybridization, the slide was placed on a 45° C. hot plate for 15 minutes; otherwise the slide did not require this step. Chemicals and slides were loaded into a VP2000 processor and the slides were passed through the following solutions: 1) 37° C. 2.0× SSC (saline sodium citrate) for 10 minutes; 2) 37° C. 0.005% pepsin working solution (pH 2.0) for 13 minutes; 3) room temperature PBS, 1% formaldehyde solution and then fresh room temperature PBS for five minutes each; 4) room temperature 70% ethanol, 85% ethanol and then 100% ethanol for two minutes each. Slides were allowed to air dry.

Denaturation/Hybridization

Four μl of the probe mixture was placed on the etched ring of the slide that contains the cells to which the probes were to be hybridized. A 12 mm circle coverslip was placed over the hybridization area and the edges of the coverslip were then sealed with a continuous bead of rubber cement. The slide was placed in a HyBrite™ denaturation/hybridization system and the canals were filled with water. Slides were heated to 73° C. for three minutes and then held at 37° C. for a minimum of eight hours.

Wash and Counterstain

Slides were taken out of the HyBrite™ and the rubber cement was removed. If the coverslip did not come off with the removal of the rubber cement, the slides were soaked in room temperature 0.1% NP-40/2.0×SSC until the coverslip fell off on its own. The slides were then placed in a Coplin jar containing 73° C. 0.1% NP-40/2.0×SSC for a minimum of two minutes. The slides were then placed in room temperature 0.1% NP-40/2.0×SSC for a minimum of five minutes. Using a pipette, 10 μl of DAPI-I counterstain (1000 ng DAPI/ml in antifade mounting solution) was applied to the hybridization ring. A 24×50 coverslip was placed atop each slide. A paper towel was placed on top of the coverslip to remove any excess liquid. The plastic end of the pipette was pressed lightly across the coverslip to remove any air bubbles. The back of each slide was wiped with a paper towel and placed in tray for analysis.

Analysis

Figure 5:
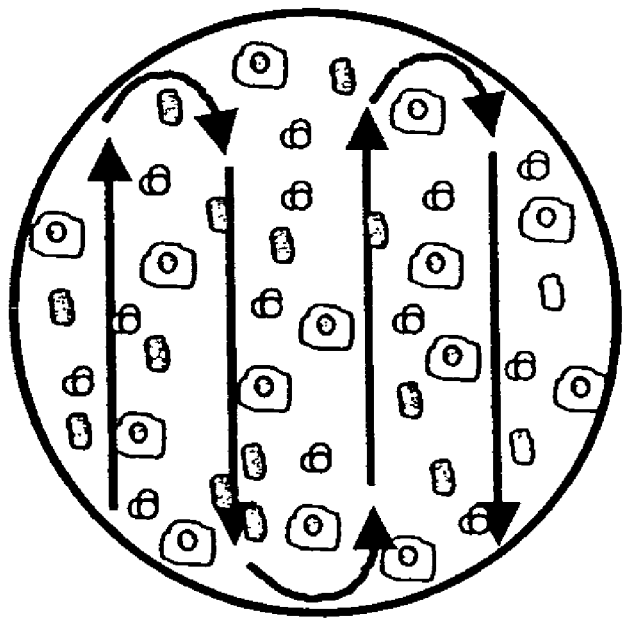
FIG. 5 shows the method used for performing a 100-cell count.

A drop of immersion oil was placed on the coverslip directly above the hybridized ring. Slides were assessed with an epi-fluorescence microscope equipped with filters to view the DAPI counterstain, Spectrum-Red/Spectrum-Green™, Spectrum-Red™, Spectrum-Green™, Spectrum-Aqua™ and Spectrum-Gold™ fluorophores. A quick initial scan of the slide was performed to assess signal quality and to determine if the hybridization was successful. The slide was then microscopically analyzed by beginning at one edge of the hybridization ring and proceeding in a systematic fashion towards the opposite end of the ring using a 40× or 63× objective (FIG. 5). The signal patterns for each of the four probes (e.g., 8q24, 9p21, 17q11, 20q13) were then recorded for one hundred consecutive non-squamous, non-inflammatory cells. In cases where only squamous cells were observed, the signal patterns were enumerated in these cells, making sure to note that only squamous cells were seen. If five or more cells with polysomy (i.e., gains of two or more of the four probes) are seen in the initial 100-cell count, no further analysis is required. However, if fewer than five cells with polysomy are observed the rest of the slide can be scanned for cells that have nuclear morphologic features suspicious for neoplasia (e.g., nuclear enlargement, nuclear irregularity, mottled chromatin staining) and the signal patterns of those cells were recorded noting that they were observed by scanning and not as part of 100-cell enumeration. Note that this scanning process is essentially identical to that described in U.S. Pat. Nos. 6,376,188 and 6,17468, which are incorporated herein by reference.

After the completion of the 100-cell enumeration, cell counts were assessed to determine if there were one or more chromosomal abnormalities present that were consistent with a diagnosis of dysplasia or EA. Chromosomal alterations that were observed and consistent with a diagnosis of either dysplasia or adenocarcinoma include: polysomy (i.e., gains of two or more signals), tetrasomy, gains of a single signal, amplification (e.g., HER-2 amplification) and deletions (e.g., 9p21 deletion).

Diagnostic Criteria.

Specimens were considered positive if they fulfilled the following criteria:
- ≧13% of cells exhibiting hemizygous and/or homozygous 9p21 loss (most consistent with a diagnosis of low-grade dysplasia)
- ≧4% of cells exhibiting gain of 8q24 (most consistent with a diagnosis of high-grade dysplasia/adenocarcinoma)
- ≧8% of cells exhibiting gain of 17q11 (most consistent with a diagnosis of high-grade dysplasia/adenocarcinoma)
- ≧16% of cells exhibiting gain of 20q13 (most consistent with a diagnosis of high-grade dysplasia/adenocarcinoma)
- ≧3% of cells exhibiting polysomy (most consistent with a diagnosis of high-grade dysplasia/adenocarcinoma)

The following representative examples show FISH enumeration results (i.e., 100-cell enumerations) and their interpretation for four patients using the four-probe FISH cocktail containing probes to 8q24, 9p21, 17q11 and 20q13. These examples illustrate how the probe-set can be used to detect dysplasia and adenocarcinoma in patients with Barrett's esophagus.

Patient 1

The one hundred-cell enumeration results for this patient are shown below (Table 7). The cells with abnormal signal patterns (i.e., cells whose signal patterns did not show two copies for each of the four probes) are shown first. The enumeration results reveal that 41 of the cells (the first 41 shown in the table) exhibited polysomy (i.e., gains of two or more of the four probes). The remaining 59 cells were considered normal. The two cells (cells 42 and 43) that didn't have the expected normal pattern of two signals per loci were not considered abnormal since the cut-off for this type of abnormality was not reached. This patient specimen was considered positive for tumor and the results are most consistent with a diagnosis of HGD/EA.

TABLE 7

Patient Specimen Considered Positive for HGD/EA

| Cell | # of Signals | | | |
|---|---|---|---|---|
| | 9p21 | 17q11 | 8q24 | 20q13 |
| 1 | 4 | 6 | 5 | 7 |
| 2 | 4 | 6 | 5 | 8 |
| 3 | 4 | 5 | 4 | 8 |
| 4 | 4 | 5 | 5 | 8 |
| 5 | 4 | 4 | 5 | 8 |
| 6 | 4 | 4 | 5 | 8 |
| 7 | 3 | 4 | 5 | 6 |
| 8 | 3 | 3 | 5 | 6 |
| 9 | 3 | 3 | 6 | 5 |
| 10 | 3 | 5 | 4 | 6 |
| 11 | 3 | 5 | 4 | 6 |
| 12 | 3 | 5 | 4 | 6 |
| 13 | 3 | 4 | 4 | 6 |
| 14 | 3 | 4 | 4 | 5 |
| 15 | 3 | 4 | 4 | 5 |
| 16 | 3 | 4 | 4 | 5 |
| 17 | 3 | 4 | 4 | 5 |
| 18 | 3 | 4 | 4 | 5 |
| 19 | 3 | 4 | 4 | 4 |
| 20 | 2 | 4 | 4 | 6 |
| 21 | 3 | 3 | 4 | 6 |
| 22 | 3 | 3 | 4 | 6 |
| 23 | 3 | 3 | 4 | 6 |
| 24 | 3 | 3 | 4 | 6 |
| 25 | 3 | 3 | 4 | 6 |
| 26 | 3 | 3 | 4 | 6 |
| 27 | 3 | 3 | 4 | 5 |
| 28 | 3 | 2 | 4 | 6 |
| 29 | 3 | 2 | 4 | 6 |
| 30 | 3 | 2 | 4 | 6 |
| 31 | 3 | 2 | 4 | 4 |
| 32 | 2 | 2 | 3 | 6 |
| 33 | 2 | 2 | 4 | 6 |
| 34 | 2 | 2 | 4 | 4 |
| 35 | 2 | 2 | 4 | 4 |
| 36 | 1 | 2 | 4 | 4 |
| 37 | 1 | 2 | 4 | 4 |
| 38 | 1 | 2 | 4 | 4 |
| 39 | 1 | 2 | 4 | 4 |
| 40 | 2 | 2 | 3 | 5 |
| 41 | 2 | 2 | 4 | 4 |
| 42 | 1 | 2 | 2 | 2 |
| 43 | 2 | 1 | 2 | 2 |
| 44 | 2 | 2 | 2 | 2 |
| 45 | 2 | 2 | 2 | 2 |
| 46 | 2 | 2 | 2 | 2 |
| 47 | 2 | 2 | 2 | 2 |
| 48 | 2 | 2 | 2 | 2 |
| 49 | 2 | 2 | 2 | 2 |
| 50 | 2 | 2 | 2 | 2 |
| 51 | 2 | 2 | 2 | 2 |
| 52 | 2 | 2 | 2 | 2 |
| 53 | 2 | 2 | 2 | 2 |
| 54 | 2 | 2 | 2 | 2 |
| 55 | 2 | 2 | 2 | 2 |
| 56 | 2 | 2 | 2 | 2 |
| 57 | 2 | 2 | 2 | 2 |
| 58 | 2 | 2 | 2 | 2 |
| 59 | 2 | 2 | 2 | 2 |
| 60 | 2 | 2 | 2 | 2 |
| 61 | 2 | 2 | 2 | 2 |
| 62 | 2 | 2 | 2 | 2 |
| 63 | 2 | 2 | 2 | 2 |
| 64 | 2 | 2 | 2 | 2 |
| 65 | 2 | 2 | 2 | 2 |
| 66 | 2 | 2 | 2 | 2 |
| 67 | 2 | 2 | 2 | 2 |
| 68 | 2 | 2 | 2 | 2 |
| 69 | 2 | 2 | 2 | 2 |
| 70 | 2 | 2 | 2 | 2 |
| 71 | 2 | 2 | 2 | 2 |
| 72 | 2 | 2 | 2 | 2 |
| 73 | 2 | 2 | 2 | 2 |
| 74 | 2 | 2 | 2 | 2 |
| 75 | 2 | 2 | 2 | 2 |
| 76 | 2 | 2 | 2 | 2 |
| 77 | 2 | 2 | 2 | 2 |
| 78 | 2 | 2 | 2 | 2 |
| 79 | 2 | 2 | 2 | 2 |

TABLE 7-continued

Patient Specimen Considered Positive for HGD/EA

| | # of Signals | | | |
|---|---|---|---|---|
| Cell | 9p21 | 17q11 | 8q24 | 20q13 |
| 80 | 2 | 2 | 2 | 2 |
| 81 | 2 | 2 | 2 | 2 |
| 82 | 2 | 2 | 2 | 2 |
| 83 | 2 | 2 | 2 | 2 |
| 84 | 2 | 2 | 2 | 2 |
| 85 | 2 | 2 | 2 | 2 |
| 86 | 2 | 2 | 2 | 2 |
| 87 | 2 | 2 | 2 | 2 |
| 88 | 2 | 2 | 2 | 2 |
| 89 | 2 | 2 | 2 | 2 |
| 90 | 2 | 2 | 2 | 2 |
| 91 | 2 | 2 | 2 | 2 |
| 92 | 2 | 2 | 2 | 2 |
| 93 | 2 | 2 | 2 | 2 |
| 94 | 2 | 2 | 2 | 2 |
| 95 | 2 | 2 | 2 | 2 |
| 96 | 2 | 2 | 2 | 2 |
| 97 | 2 | 2 | 2 | 2 |
| 98 | 2 | 2 | 2 | 2 |
| 99 | 2 | 2 | 2 | 2 |
| 100 | 2 | 2 | 2 | 2 |

*Polysomic cells are in bold

Patient 2

The one hundred-cell enumeration results for this patient are shown below (Table 8). The cells with abnormal signal patterns (i.e., cells whose signal patterns did not show two copies for each of the four probes) are shown first. The enumeration results reveal 23 cells with a gain of 8q24. The remaining 77 cells were considered normal. This patient specimen was considered positive and the results are most consistent with a diagnosis of HGD/EA.

TABLE 8

Patient Specimen Considered Positive for HGD/EA

| | # of Signals | | | |
|---|---|---|---|---|
| Cell | 9p21 | 17q11 | 8q24 | 20q13 |
| 1 | 1 | 2 | 5 | 2 |
| 2 | 1 | 2 | 4 | 2 |
| 3 | 2 | 2 | 4 | 2 |
| 4 | 2 | 2 | 4 | 2 |
| 5 | 1 | 2 | 3 | 2 |
| 6 | 2 | 1 | 3 | 2 |
| 7 | 2 | 2 | 3 | 2 |
| 8 | 2 | 2 | 3 | 2 |
| 9 | 2 | 2 | 3 | 2 |
| 10 | 2 | 2 | 3 | 2 |
| 11 | 2 | 2 | 3 | 2 |
| 12 | 2 | 2 | 3 | 2 |
| 13 | 2 | 2 | 3 | 2 |
| 14 | 2 | 2 | 3 | 2 |
| 15 | 2 | 2 | 3 | 2 |
| 16 | 2 | 2 | 3 | 2 |
| 17 | 2 | 2 | 3 | 2 |
| 18 | 2 | 2 | 3 | 2 |
| 19 | 2 | 2 | 3 | 2 |
| 20 | 2 | 2 | 3 | 2 |
| 21 | 2 | 2 | 3 | 2 |
| 22 | 2 | 2 | 3 | 2 |
| 23 | 2 | 2 | 3 | 2 |
| 24 | 2 | 2 | 2 | 2 |
| 25 | 2 | 2 | 2 | 2 |
| 26 | 2 | 2 | 2 | 2 |
| 27 | 2 | 2 | 2 | 2 |
| 28 | 2 | 2 | 2 | 2 |
| 29 | 2 | 2 | 2 | 2 |
| 30 | 2 | 2 | 2 | 2 |
| 31 | 2 | 2 | 2 | 2 |
| 32 | 2 | 2 | 2 | 2 |
| 33 | 2 | 2 | 2 | 2 |
| 34 | 2 | 2 | 2 | 2 |
| 35 | 2 | 2 | 2 | 2 |
| 36 | 2 | 2 | 2 | 2 |
| 37 | 2 | 2 | 2 | 2 |
| 38 | 2 | 2 | 2 | 2 |
| 39 | 2 | 2 | 2 | 2 |
| 40 | 2 | 2 | 2 | 2 |
| 41 | 2 | 2 | 2 | 2 |
| 42 | 2 | 2 | 2 | 2 |
| 43 | 2 | 2 | 2 | 2 |
| 44 | 2 | 2 | 2 | 2 |
| 45 | 2 | 2 | 2 | 2 |
| 46 | 2 | 2 | 2 | 2 |
| 47 | 2 | 2 | 2 | 2 |
| 48 | 2 | 2 | 2 | 2 |
| 49 | 2 | 2 | 2 | 2 |
| 50 | 2 | 2 | 2 | 2 |
| 51 | 2 | 2 | 2 | 2 |
| 52 | 2 | 2 | 2 | 2 |
| 53 | 2 | 2 | 2 | 2 |
| 54 | 2 | 2 | 2 | 2 |
| 55 | 2 | 2 | 2 | 2 |
| 56 | 2 | 2 | 2 | 2 |
| 57 | 2 | 2 | 2 | 2 |
| 58 | 2 | 2 | 2 | 2 |
| 59 | 2 | 2 | 2 | 2 |
| 60 | 2 | 2 | 2 | 2 |
| 61 | 2 | 2 | 2 | 2 |
| 62 | 2 | 2 | 2 | 2 |
| 63 | 2 | 2 | 2 | 2 |
| 64 | 2 | 2 | 2 | 2 |
| 65 | 2 | 2 | 2 | 2 |
| 66 | 2 | 2 | 2 | 2 |
| 67 | 2 | 2 | 2 | 2 |
| 68 | 2 | 2 | 2 | 2 |
| 69 | 2 | 2 | 2 | 2 |
| 70 | 2 | 2 | 2 | 2 |
| 71 | 2 | 2 | 2 | 2 |
| 72 | 2 | 2 | 2 | 2 |
| 73 | 2 | 2 | 2 | 2 |
| 74 | 2 | 2 | 2 | 2 |
| 75 | 2 | 2 | 2 | 2 |
| 76 | 2 | 2 | 2 | 2 |
| 77 | 2 | 2 | 2 | 2 |
| 78 | 2 | 2 | 2 | 2 |
| 79 | 2 | 2 | 2 | 2 |
| 80 | 2 | 2 | 2 | 2 |
| 81 | 2 | 2 | 2 | 2 |
| 82 | 2 | 2 | 2 | 2 |
| 83 | 2 | 2 | 2 | 2 |
| 84 | 2 | 2 | 2 | 2 |
| 85 | 2 | 2 | 2 | 2 |
| 86 | 2 | 2 | 2 | 2 |
| 87 | 2 | 2 | 2 | 2 |
| 88 | 2 | 2 | 2 | 2 |
| 89 | 2 | 2 | 2 | 2 |
| 90 | 2 | 2 | 2 | 2 |
| 91 | 2 | 2 | 2 | 2 |
| 92 | 2 | 2 | 2 | 2 |
| 93 | 2 | 2 | 2 | 2 |
| 94 | 2 | 2 | 2 | 2 |
| 95 | 2 | 2 | 2 | 2 |
| 96 | 2 | 2 | 2 | 2 |
| 97 | 2 | 2 | 2 | 2 |
| 98 | 2 | 2 | 2 | 2 |
| 99 | 2 | 2 | 2 | 2 |
| 100 | 2 | 2 | 2 | 2 |

*Cells with a gain of the 8q24 probe are in bold

Patient 3

The one hundred-cell enumeration results for this patient are shown below (Table 9). The cells with abnormal signal patterns (i.e., cells whose signal patterns did not show two copies for each of the four probes) are shown first. The enumeration results reveal that 52 of the cells (the first 52 shown in the table) exhibited either homozygous or hemizygous 9p21 loss. The remaining 48 cells were considered normal. Cell 53 which had a signal pattern of 2,2,1,2 didn't have the expected normal pattern of two signals per loci but was considered normal since the cut-off for this type of abnormality (i.e., monosomy 8q24) was not reached. This patient specimen was considered positive and the results are most consistent with a diagnosis of LGD.

TABLE 9

Patient Specimen Considered Positive for LGD

| Cell | # of Signals | | | |
|---|---|---|---|---|
| | 9p21 | 17q11 | 8q24 | 20q13 |
| 1 | 0 | 1 | 2 | 2 |
| 2 | 0 | 2 | 2 | 2 |
| 3 | 0 | 2 | 2 | 2 |
| 4 | 0 | 2 | 2 | 2 |
| 5 | 0 | 2 | 2 | 2 |
| 6 | 0 | 2 | 2 | 2 |
| 7 | 0 | 2 | 2 | 2 |
| 8 | 0 | 2 | 2 | 2 |
| 9 | 0 | 2 | 2 | 2 |
| 10 | 0 | 2 | 2 | 2 |
| 11 | 0 | 2 | 2 | 2 |
| 12 | 0 | 2 | 2 | 2 |
| 13 | 0 | 2 | 2 | 2 |
| 14 | 0 | 2 | 2 | 2 |
| 15 | 0 | 2 | 2 | 2 |
| 16 | 1 | 1 | 2 | 2 |
| 17 | 1 | 2 | 1 | 2 |
| 18 | 1 | 2 | 2 | 2 |
| 19 | 1 | 2 | 2 | 2 |
| 20 | 1 | 2 | 2 | 2 |
| 21 | 1 | 2 | 2 | 2 |
| 22 | 1 | 2 | 2 | 2 |
| 23 | 1 | 2 | 2 | 2 |
| 24 | 1 | 2 | 2 | 2 |
| 25 | 1 | 2 | 2 | 2 |
| 26 | 1 | 2 | 2 | 2 |
| 27 | 1 | 2 | 2 | 2 |
| 28 | 1 | 2 | 2 | 2 |
| 29 | 1 | 2 | 2 | 2 |
| 30 | 1 | 2 | 2 | 2 |
| 31 | 1 | 2 | 2 | 2 |
| 32 | 1 | 2 | 2 | 2 |
| 33 | 1 | 2 | 2 | 2 |
| 34 | 1 | 2 | 2 | 2 |
| 35 | 1 | 2 | 2 | 2 |
| 36 | 1 | 2 | 2 | 2 |
| 37 | 1 | 2 | 2 | 2 |
| 38 | 1 | 2 | 2 | 2 |
| 39 | 1 | 2 | 2 | 2 |
| 40 | 1 | 2 | 2 | 2 |
| 41 | 1 | 2 | 2 | 2 |
| 42 | 1 | 2 | 2 | 2 |
| 43 | 1 | 2 | 2 | 2 |
| 44 | 1 | 2 | 2 | 2 |
| 45 | 1 | 2 | 2 | 2 |
| 46 | 1 | 2 | 2 | 2 |
| 47 | 1 | 2 | 2 | 2 |
| 48 | 1 | 2 | 2 | 2 |
| 49 | 1 | 2 | 2 | 2 |
| 50 | 1 | 2 | 2 | 2 |
| 51 | 1 | 2 | 2 | 2 |
| 52 | 1 | 2 | 2 | 2 |
| 53 | 2 | 2 | 1 | 2 |
| 54 | 2 | 2 | 2 | 2 |
| 55 | 2 | 2 | 2 | 2 |

TABLE 9-continued

Patient Specimen Considered Positive for LGD

| Cell | # of Signals | | | |
|---|---|---|---|---|
| | 9p21 | 17q11 | 8q24 | 20q13 |
| 56 | 2 | 2 | 2 | 2 |
| 57 | 2 | 2 | 2 | 2 |
| 58 | 2 | 2 | 2 | 2 |
| 59 | 2 | 2 | 2 | 2 |
| 60 | 2 | 2 | 2 | 2 |
| 61 | 2 | 2 | 2 | 2 |
| 62 | 2 | 2 | 2 | 2 |
| 63 | 2 | 2 | 2 | 2 |
| 64 | 2 | 2 | 2 | 2 |
| 65 | 2 | 2 | 2 | 2 |
| 66 | 2 | 2 | 2 | 2 |
| 67 | 2 | 2 | 2 | 2 |
| 68 | 2 | 2 | 2 | 2 |
| 69 | 2 | 2 | 2 | 2 |
| 70 | 2 | 2 | 2 | 2 |
| 71 | 2 | 2 | 2 | 2 |
| 72 | 2 | 2 | 2 | 2 |
| 73 | 2 | 2 | 2 | 2 |
| 74 | 2 | 2 | 2 | 2 |
| 75 | 2 | 2 | 2 | 2 |
| 76 | 2 | 2 | 2 | 2 |
| 77 | 2 | 2 | 2 | 2 |
| 78 | 2 | 2 | 2 | 2 |
| 79 | 2 | 2 | 2 | 2 |
| 80 | 2 | 2 | 2 | 2 |
| 81 | 2 | 2 | 2 | 2 |
| 82 | 2 | 2 | 2 | 2 |
| 83 | 2 | 2 | 2 | 2 |
| 84 | 2 | 2 | 2 | 2 |
| 85 | 2 | 2 | 2 | 2 |
| 86 | 2 | 2 | 2 | 2 |
| 87 | 2 | 2 | 2 | 2 |
| 88 | 2 | 2 | 2 | 2 |
| 89 | 2 | 2 | 2 | 2 |
| 90 | 2 | 2 | 2 | 2 |
| 91 | 2 | 2 | 2 | 2 |
| 92 | 2 | 2 | 2 | 2 |
| 93 | 2 | 2 | 2 | 2 |
| 94 | 2 | 2 | 2 | 2 |
| 95 | 2 | 2 | 2 | 2 |
| 96 | 2 | 2 | 2 | 2 |
| 97 | 2 | 2 | 2 | 2 |
| 98 | 2 | 2 | 2 | 2 |
| 99 | 2 | 2 | 2 | 2 |
| 100 | 2 | 2 | 2 | 2 |

*Cells with a loss of 9p21 are in bold

Patient 4

The one hundred-cell enumeration results for this patient are shown below (Table 0). The cells with abnormal signal patterns (i.e., cells whose signal patterns did not show two copies for each of the four probes) are shown first. The enumeration results reveal three cells (cells 1-3) that didn't have the expected normal pattern of two signals per loci, however, these cells were not considered abnormal since the cut-off for any abnormalities was not reached. This patient specimen was considered negative.

TABLE 10

Patient Specimen Considered Negative

| Cell | # of Signals | | | |
|---|---|---|---|---|
| | 9p21 | 17q11 | 8q24 | 20q13 |
| 1 | 1 | 1 | 2 | 2 |
| 2 | 2 | 1 | 2 | 2 |
| 3 | 2 | 2 | 2 | 1 |
| 4 | 2 | 2 | 2 | 2 |

TABLE 10-continued

Patient Specimen Considered Negative

| Cell | # of Signals | | | |
|---|---|---|---|---|
| | 9p21 | 17q11 | 8q24 | 20q13 |
| 5 | 2 | 2 | 2 | 2 |
| 6 | 2 | 2 | 2 | 2 |
| 7 | 2 | 2 | 2 | 2 |
| 8 | 2 | 2 | 2 | 2 |
| 9 | 2 | 2 | 2 | 2 |
| 10 | 2 | 2 | 2 | 2 |
| 11 | 2 | 2 | 2 | 2 |
| 12 | 2 | 2 | 2 | 2 |
| 13 | 2 | 2 | 2 | 2 |
| 14 | 2 | 2 | 2 | 2 |
| 15 | 2 | 2 | 2 | 2 |
| 16 | 2 | 2 | 2 | 2 |
| 17 | 2 | 2 | 2 | 2 |
| 18 | 2 | 2 | 2 | 2 |
| 19 | 2 | 2 | 2 | 2 |
| 20 | 2 | 2 | 2 | 2 |
| 21 | 2 | 2 | 2 | 2 |
| 22 | 2 | 2 | 2 | 2 |
| 23 | 2 | 2 | 2 | 2 |
| 24 | 2 | 2 | 2 | 2 |
| 25 | 2 | 2 | 2 | 2 |
| 26 | 2 | 2 | 2 | 2 |
| 27 | 2 | 2 | 2 | 2 |
| 28 | 2 | 2 | 2 | 2 |
| 29 | 2 | 2 | 2 | 2 |
| 30 | 2 | 2 | 2 | 2 |
| 31 | 2 | 2 | 2 | 2 |
| 32 | 2 | 2 | 2 | 2 |
| 33 | 2 | 2 | 2 | 2 |
| 34 | 2 | 2 | 2 | 2 |
| 35 | 2 | 2 | 2 | 2 |
| 36 | 2 | 2 | 2 | 2 |
| 37 | 2 | 2 | 2 | 2 |
| 38 | 2 | 2 | 2 | 2 |
| 39 | 2 | 2 | 2 | 2 |
| 40 | 2 | 2 | 2 | 2 |
| 41 | 2 | 2 | 2 | 2 |
| 42 | 2 | 2 | 2 | 2 |
| 43 | 2 | 2 | 2 | 2 |
| 44 | 2 | 2 | 2 | 2 |
| 45 | 2 | 2 | 2 | 2 |
| 46 | 2 | 2 | 2 | 2 |
| 47 | 2 | 2 | 2 | 2 |
| 48 | 2 | 2 | 2 | 2 |
| 49 | 2 | 2 | 2 | 2 |
| 50 | 2 | 2 | 2 | 2 |
| 51 | 2 | 2 | 2 | 2 |
| 52 | 2 | 2 | 2 | 2 |
| 53 | 2 | 2 | 2 | 2 |
| 54 | 2 | 2 | 2 | 2 |
| 55 | 2 | 2 | 2 | 2 |
| 56 | 2 | 2 | 2 | 2 |
| 57 | 2 | 2 | 2 | 2 |
| 58 | 2 | 2 | 2 | 2 |
| 59 | 2 | 2 | 2 | 2 |
| 60 | 2 | 2 | 2 | 2 |
| 61 | 2 | 2 | 2 | 2 |
| 62 | 2 | 2 | 2 | 2 |
| 63 | 2 | 2 | 2 | 2 |
| 64 | 2 | 2 | 2 | 2 |
| 65 | 2 | 2 | 2 | 2 |
| 66 | 2 | 2 | 2 | 2 |
| 67 | 2 | 2 | 2 | 2 |
| 68 | 2 | 2 | 2 | 2 |
| 69 | 2 | 2 | 2 | 2 |
| 70 | 2 | 2 | 2 | 2 |
| 71 | 2 | 2 | 2 | 2 |
| 72 | 2 | 2 | 2 | 2 |
| 73 | 2 | 2 | 2 | 2 |
| 74 | 2 | 2 | 2 | 2 |
| 75 | 2 | 2 | 2 | 2 |
| 76 | 2 | 2 | 2 | 2 |
| 77 | 2 | 2 | 2 | 2 |
| 78 | 2 | 2 | 2 | 2 |
| 79 | 2 | 2 | 2 | 2 |
| 80 | 2 | 2 | 2 | 2 |
| 81 | 2 | 2 | 2 | 2 |
| 82 | 2 | 2 | 2 | 2 |
| 83 | 2 | 2 | 2 | 2 |
| 84 | 2 | 2 | 2 | 2 |
| 85 | 2 | 2 | 2 | 2 |
| 86 | 2 | 2 | 2 | 2 |
| 87 | 2 | 2 | 2 | 2 |
| 88 | 2 | 2 | 2 | 2 |
| 89 | 2 | 2 | 2 | 2 |
| 90 | 2 | 2 | 2 | 2 |
| 91 | 2 | 2 | 2 | 2 |
| 92 | 2 | 2 | 2 | 2 |
| 93 | 2 | 2 | 2 | 2 |
| 94 | 2 | 2 | 2 | 2 |
| 95 | 2 | 2 | 2 | 2 |
| 96 | 2 | 2 | 2 | 2 |
| 97 | 2 | 2 | 2 | 2 |
| 98 | 2 | 2 | 2 | 2 |
| 99 | 2 | 2 | 2 | 2 |
| 100 | 2 | 2 | 2 | 2 |

Other Embodiments

It is to be understood that, while the invention has been described in conjunction with the detailed description, thereof, the foregoing description is intended to illustrate and not limit the scope of the invention. Other aspects, advantages, and modifications of the invention are within the scope of the claims set forth below.

What is claimed is:

1. A method for screening for an esophageal carcinoma or precursor lesion in a human subject whose status with respect to esophageal carcinoma is unknown, the method comprising:
   a. obtaining a biological sample comprising esophageal cells from the subject;
   b. contacting the sample with a set of three or more chromosomal probes selected from the group consisting of an 8q24.12-13 locus-specific probe, a 7p12 locus-specific probe, a 17q11.2-12 locus-specific probe, a 20q13 locus-specific probe, a chromosome enumeration probe for chromosome 9, a chromosome enumeration probe for chromosome 7, a 5q21-22 locus-specific probe, a 5p15 locus-specific probe, a 17p13.1 locus-specific probe, a chromosome enumeration probe for chromosome 17 and a 9p21 locus-specific probe to selectively detect an esophageal carcinoma or precursor lesion in the sample, if any, under conditions for specifically hybridizing the probes to their nucleic acid targets present in the sample, wherein at least one of the probes in the probe set is an 8q24.12-13 locus specific probe, a chromosome enumeration probe for chromosome 7 or a 17p13.1 locus specific probe; and
   c. detecting a hybridization pattern evaluating gains and losses for the set of chromosomal probes to the biological sample, wherein the hybridization pattern is indicative for the presence or absence of an esophageal carcinoma or precursor lesion in the subject.

2. The method of claim 1 wherein the carcinoma precursor lesion selectively detected is low-grade dysplasia (LGD).

3. The method of claim 1 wherein the carcinoma or precursor lesion selectively detected is selected from the group consisting of high-grade dysplasia (HGD) and esophageal adenocarcinoma (EA).

4. The method of claim 1 wherein the biological sample comprises cells obtained from a specimen selected from the group consisting of a biopsy, a cytologic specimen and a resected specimen.

5. The method of claim 1 wherein the chromosomal probes are fluorescently labeled.

6. The method of claim 4 wherein the biological sample comprises a cytologic brushing specimen.

7. The method of claim 1 wherein the subject has been diagnosed with a condition selected from the group consisting of chronic gastroesophageal reflux disease and Barrett's esophagus.

8. The method of claim 2 wherein the set of chromosomal probes is characterized by a DFI of about 0.7 or below for said precursor lesion.

9. The method of claim 8 wherein the set of chromosomal probes is characterized by a DFI of about 0.35 or below for said precursor lesion.

10. The method of claim 3 wherein the set of chromosomal probes is characterized by a DFI of about 0.5 or below for said esophageal carcinoma or precursor lesion.

11. The method of claim 10 wherein the set of chromosomal probes is characterized by a DFI of about 0.35 or below for said precursor lesion.

12. The method of claim 1 wherein said set further comprises a chromosome enumeration probe for the Y chromosome.

13. The method of claim 1 wherein said set comprises at least one chromosome enumeration probe.

14. The method of claim 1 wherein said set consists of a 20q13 locus-specific probe, a 17q11.2-12 locus-specific probe, a 9p21 locus-specific probe, and an 8q24.12-13 locus-specific probe.

15. The method of claim 1 wherein the hybridization pattern is detected in cells from the biological sample that are pre-selected for on the basis of abnormalities in nuclear size, nuclear shape or nuclear staining.

16. The method of claim 1 wherein the biological sample is embedded in paraffin.

* * * * *

UNITED STATES PATENT AND TRADEMARK OFFICE
CERTIFICATE OF CORRECTION

PATENT NO. : 8,034,577 B2  
APPLICATION NO. : 11/356786  
DATED : October 11, 2011  
INVENTOR(S) : Kevin Halling, Larry E. Morrison and Shannon Brankley It is certified that error appears in the above-identified patent and that said Letters Patent is hereby corrected as shown below:

Title Page, Item (73)

"Assignees: Mayo Foundation for Medical Education and Research, Rochester, MN (US); Abbott Laboratories, Inc., Des Plaines, IL (US)"

be corrected to:

--Assignees: Mayo Foundation for Medical Education and Research, Rochester, MN (US); Abbott Laboratories, Des Plaines, IL (US)--

Signed and Sealed this  
Eighth Day of May, 2012

David J. Kappos  
*Director of the United States Patent and Trademark Office*

UNITED STATES PATENT AND TRADEMARK OFFICE
CERTIFICATE OF CORRECTION

PATENT NO.        : 8,034,577 B2
APPLICATION NO.   : 11/356786
DATED             : October 11, 2011
INVENTOR(S)       : Kevin Halling et al.

Page 1 of 1

It is certified that error appears in the above-identified patent and that said Letters Patent is hereby corrected as shown below:

Column 42 part of Claim 1, Line 61 please revise "c. detecting a hybridization pattern evaluating gains and" to read as --c. detecting a hybridization pattern for gains and--

Signed and Sealed this
Fifth Day of February, 2013

Teresa Stanek Rea
*Acting Director of the United States Patent and Trademark Office*